United States Patent
Bhatnagar et al.

(10) Patent No.: US 11,259,740 B2
(45) Date of Patent: Mar. 1, 2022

(54) METHODS USEFUL IN OPTIMIZING THE TREATMENT OF NEUROPATHIES AND TARGETING TISSUES WITH COSMETIC BOTULINUM INJECTIONS

(71) Applicant: The Research Foundation for The State University of New York, Albany, NY (US)

(72) Inventors: Divya Bhatnagar, Stony Brook, NY (US); Miriam Rafailovich, Plainview, NY (US); Raphael Davis, Port Jefferson, NY (US); Alexander B. Dagum, Stony Brook, NY (US); Duc T. Bui, Dix Hills, NY (US)

(73) Assignee: The Research Foundation for State University of New York, Albany, NY (US)

( * ) Notice: Subject to any disclaimer, the term of this patent is extended or adjusted under 35 U.S.C. 154(b) by 261 days.

(21) Appl. No.: 15/944,528

(22) Filed: Apr. 3, 2018

(65) Prior Publication Data

US 2018/0220951 A1 Aug. 9, 2018

Related U.S. Application Data

(63) Continuation of application No. 13/463,766, filed on May 3, 2012, now abandoned.
(Continued)

(51) Int. Cl.
*A61B 5/00* (2006.01)
*A61B 5/11* (2006.01)

(52) U.S. Cl.
CPC ............ *A61B 5/442* (2013.01); *A61B 5/1107* (2013.01); *A61B 5/1128* (2013.01); *A61B 5/4041* (2013.01); *A61B 5/4839* (2013.01)

(58) Field of Classification Search
CPC ..... A61B 5/442; A61B 5/4041; A61B 5/1107; A61B 5/1128; A61B 5/4839
See application file for complete search history.

(56) References Cited

U.S. PATENT DOCUMENTS

| | | |
|---|---|---|
| 5,183,462 A | 2/1993 | Borodic |
| 5,401,243 A | 3/1995 | Borodic |
| (Continued) | | |

FOREIGN PATENT DOCUMENTS

| | | |
|---|---|---|
| EP | 2460875 A1 | 6/2012 |
| WO | 2003091387 A2 | 11/2003 |
| (Continued) | | |

OTHER PUBLICATIONS

Staloff et al. 2008 Skin Res.Technol. 14:127-134 (Year: 2008).*
(Continued)

*Primary Examiner* — Pascal M Bui Pho
*Assistant Examiner* — Patrick M Mehl
(74) *Attorney, Agent, or Firm* — Fox Rothschild LLP

(57) ABSTRACT

The present invention pertains to methods of determining where, on the skin, a diagnostic, therapeutic, or cosmetic agent is likely to be most effectively applied (e.g., injected), and to methods for monitoring a patient after such an agent has been administered. The monitoring can produce information useful in determining whether a diagnostic, therapeutic (e.g., surgical), or cosmetic regime should be initiated, continued, continued in a modified fashion, or terminated (e.g., for a brief or prolonged period of time). The methods can be repeated periodically and use a non-invasive, in vivo form of digital image speckle correlation (DISC) to track deformation of the skin.

13 Claims, 33 Drawing Sheets

Related U.S. Application Data

(60) Provisional application No. 61/482,057, filed on May 3, 2011.

(56) References Cited

U.S. PATENT DOCUMENTS

| | | | |
|---|---|---|---|
| 7,795,218 | B2 | 9/2010 | McKerracher et al. |
| 7,981,866 | B2 | 7/2011 | Ma et al. |
| 8,106,251 | B2 | 1/2012 | Ayares et al. |
| 8,206,299 | B2 | 6/2012 | Foley et al. |
| 8,318,181 | B2 | 11/2012 | Edelson et al. |
| 8,641,696 | B2 | 2/2014 | Barbour |
| 8,658,391 | B2 | 2/2014 | Edelson |
| 8,709,402 | B2 | 4/2014 | Emig et al. |
| 8,912,142 | B2 | 12/2014 | Sprecher et al. |
| 8,918,162 | B2 | 12/2014 | Prokoski |
| 8,974,774 | B2 | 3/2015 | Dake et al. |
| 9,295,691 | B2 | 3/2016 | Boutros |
| 9,408,881 | B2 | 8/2016 | Gruber et al. |
| 9,499,791 | B2 | 11/2016 | Payne et al. |
| 10,113,166 | B2 | 10/2018 | Collard et al. |
| 10,532,019 | B2 | 1/2020 | Edelson et al. |
| 10,588,694 | B1 | 3/2020 | Neev |
| 10,722,562 | B2 | 7/2020 | Pedersen et al. |
| 2003/0036502 | A1 | 2/2003 | Gassner et al. |
| 2004/0060569 | A1 | 4/2004 | Hanin |
| 2004/0220100 | A1 | 11/2004 | Waugh et al. |
| 2005/0191242 | A1 | 9/2005 | Brissette et al. |
| 2005/0240126 | A1 | 10/2005 | Foley et al. |
| 2007/0140968 | A1 | 6/2007 | Hanin et al. |
| 2007/0154529 | A1 | 7/2007 | Bullerdiek |
| 2007/0248590 | A1 | 10/2007 | Milne et al. |
| 2008/0200373 | A1 | 8/2008 | Waugh et al. |
| 2009/0022665 | A1* | 1/2009 | Isabelle .............. A61K 49/0006 424/9.1 |
| 2009/0155314 | A1* | 6/2009 | Tezel ...................... A61K 8/64 424/239.1 |
| 2009/0226424 | A1 | 9/2009 | Hsu |
| 2010/0028306 | A1 | 2/2010 | Clarke et al. |
| 2011/0177025 | A1 | 7/2011 | Thanos et al. |
| 2011/0212157 | A1 | 9/2011 | Edelson et al. |
| 2012/0251510 | A1 | 10/2012 | Tamai et al. |
| 2012/0301444 | A1 | 11/2012 | Clarke et al. |
| 2012/0309051 | A1 | 12/2012 | Ma et al. |
| 2020/0115425 | A1 | 4/2020 | Gallego-Perez et al. |

FOREIGN PATENT DOCUMENTS

| | | |
|---|---|---|
| WO | 2006092668 A2 | 9/2006 |
| WO | 2007067536 A1 | 6/2007 |
| WO | 2010003643 A1 | 1/2010 |

OTHER PUBLICATIONS

Mahadevappa et al. 2010 Med.Hypo. 74:508-509 (Year: 2010).*
Mitre et al. 2008 Am.J.O.R.L.-N.H. Med.Surg. 29:51-57 (Year: 2008).*
Manni e tal 2001 Am. J. Surg. 182:268-273 (Year: 2001).*
McElveen et al. 2000 The Laryngoscope 110:1667-1672 (Year: 2000).*
Mehta et al. 2008 Arch.Facial Plast.Surg. 10:84-87 (Year: 2008).*
Polo 2008 Am.J. Orthodontics Dentofacial Orthopedics 133:195-203 (Year: 2008).*
Sarrabayrouse 2002 Aesth.Plast.Surg. 26:233-238 (Year: 2002).*
Lees 1992 BMJ London 305:1169-1170 (Year: 1922).*
Verma et al. 2019 Plast. Reconstr. Surg. 143:1614-1618 (Year: 2019).*
Mahadevappa, K. et al., "Facial Paralysis: A Critical Review of Accepted Explanation", Med. Hypo (2010); vol. 74, pp. 508-509.
Mcelveen, Jr., J. T., et al., "A Review of Facial Nerve Outcome in 100 Consecutive Cases of Acoustic Tumor Surgery", The Laryngoscope (2000); vol. 110, pp. 1667-1672.
Metha, R. P et al., "Botulinum Toxin and Quality of Life in Patients with Facial Paralysis", Arch. Facial Plast. Surg. (2008); vol. 10:2, pp. 84-87.
Mitre, E.I., et al., Objective Method of Facial Motricity Grading in Healthy Individuals and in Patients with Unilateral.
Polo, M., "Botulinum Toxin Type A (Botox) for the Neuromuscular Correction of Excessive Gingival Display on Smiling (gummy smile)", Am. J. of Orthodontics Dentofacial Orthopedics (2008); vol. 133, pp. 195-203.
Sarrabayrouse, M., "Indications and Limitations for the Use of Botulinum Toxin for the Treatment of Facial Wrinkles", Aesth. Plast. Surg. (2002); vol. 26, pp. 233-238.
Staloff, I. A. et al., "An in vivo Study of the Mechanical Properties of Facial Skin and Influence of Aging Using Digital Image Speckle Correlation", Skin Res. and Tech. (2008); vol. 14, pp. 127-134.
Staloff, I.A., et al., "Measurement of Skin Stretch using Digital Image Speckle Correlation", Skin Res. and Tech. (2008), vol. 14, pp. 298-303.

* cited by examiner

Photographs and Analysis

- For Botox, Patients are photographed with their faces at rest and during a small movement
    - Raising Eyebrows (Forehead)
    - Frowning (Glabella)
    - Blinking (Crow's Feet)
- Photos are taken at T=0, 1 week, 2 weeks, 4 weeks, and monthly to 6 months
- Digital photos are analyzed using DISC and facial muscle contraction is quantified and compared to baseline
- Quantitative analysis is corroborated with FLO-11®, SPA® Measure, and SGA (physician and patient) scores

- For Acoustic Neuroma Study, Patients were photographed with their faces at rest and during a small movement: Smile
- Photos are taken either Post surgery or Pre surgery.
- DISC is then used to analyze the digital photos

FIG. 1

Frowning: Patient 1(BOTOX Study Group)

Frowning: Patient 1(BOTOX Study Group)

Frowning: Patient 1(BOTOX Study Group)
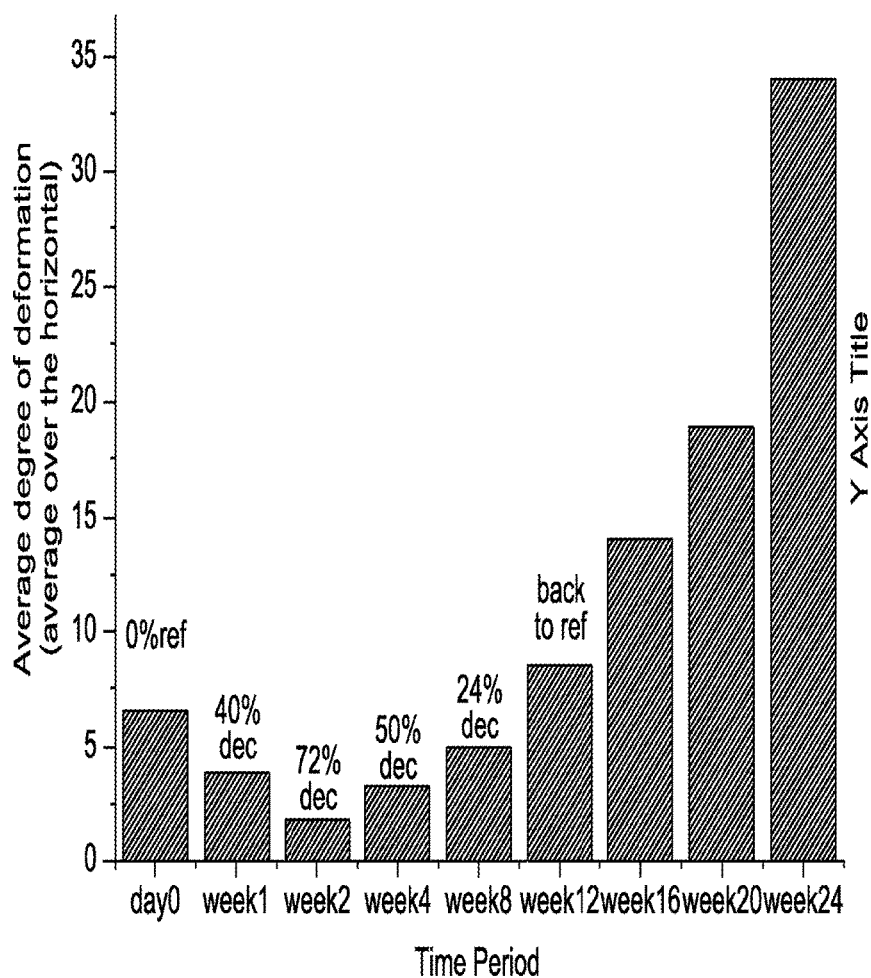
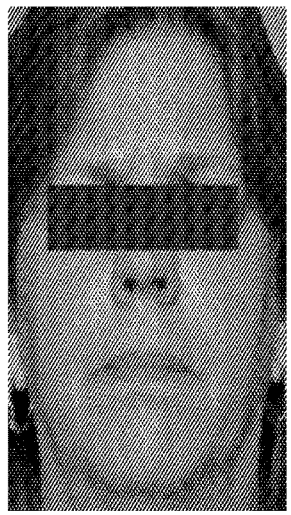
FIG. 2(Cont.)

Frowning: Patient 2

Frowning: Patient 2

Frowning: Patient 2

Frowning: Patient 2

Frowning: Patient 2

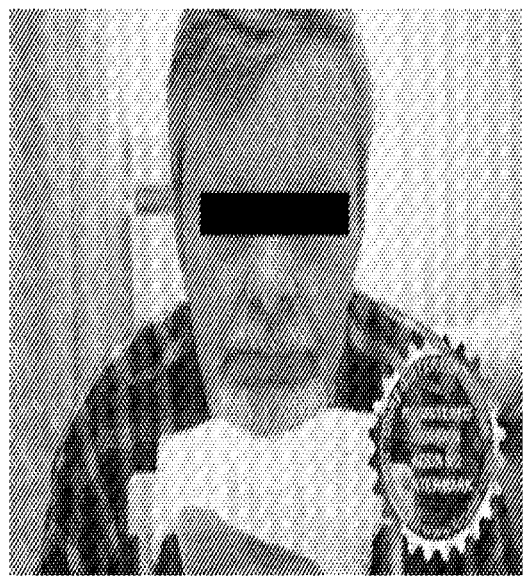
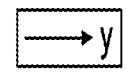
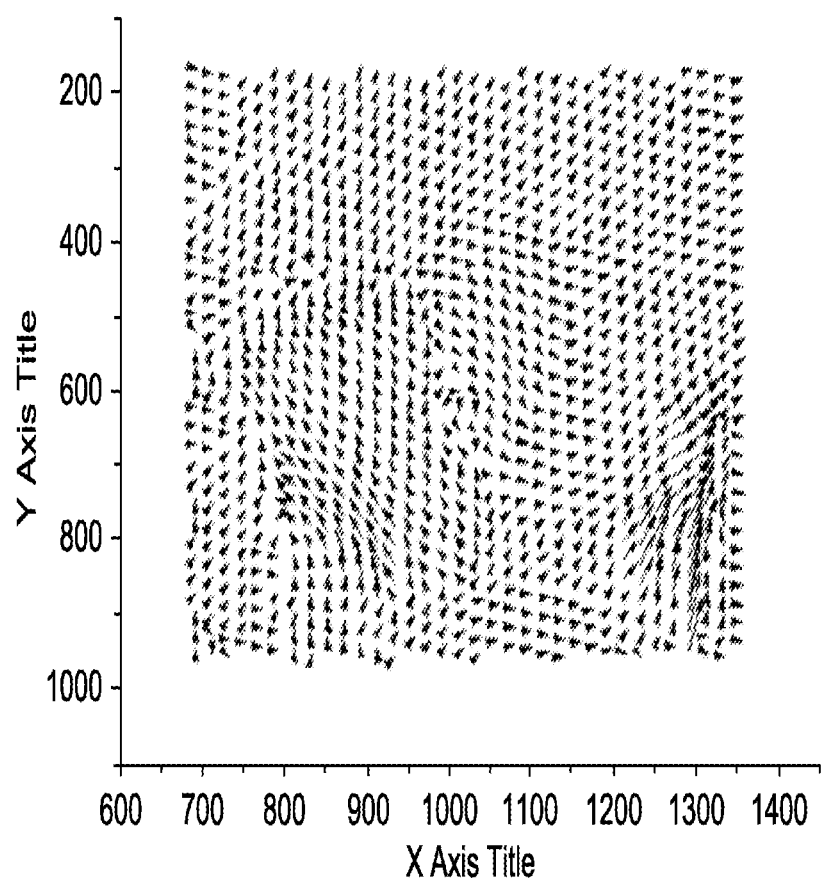
FIG. 6

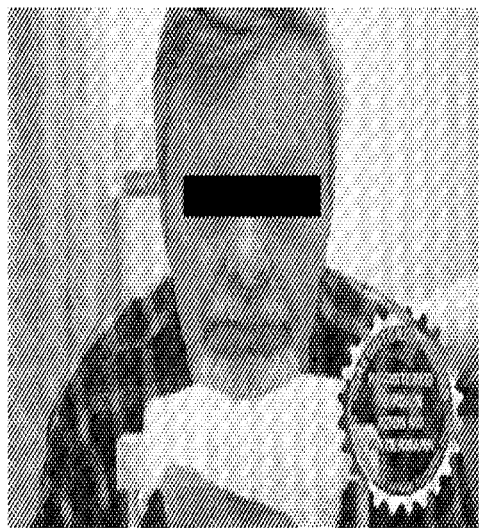
Subject 2: Post op(2005)
Neuroma: Left ; Size(mm): 6
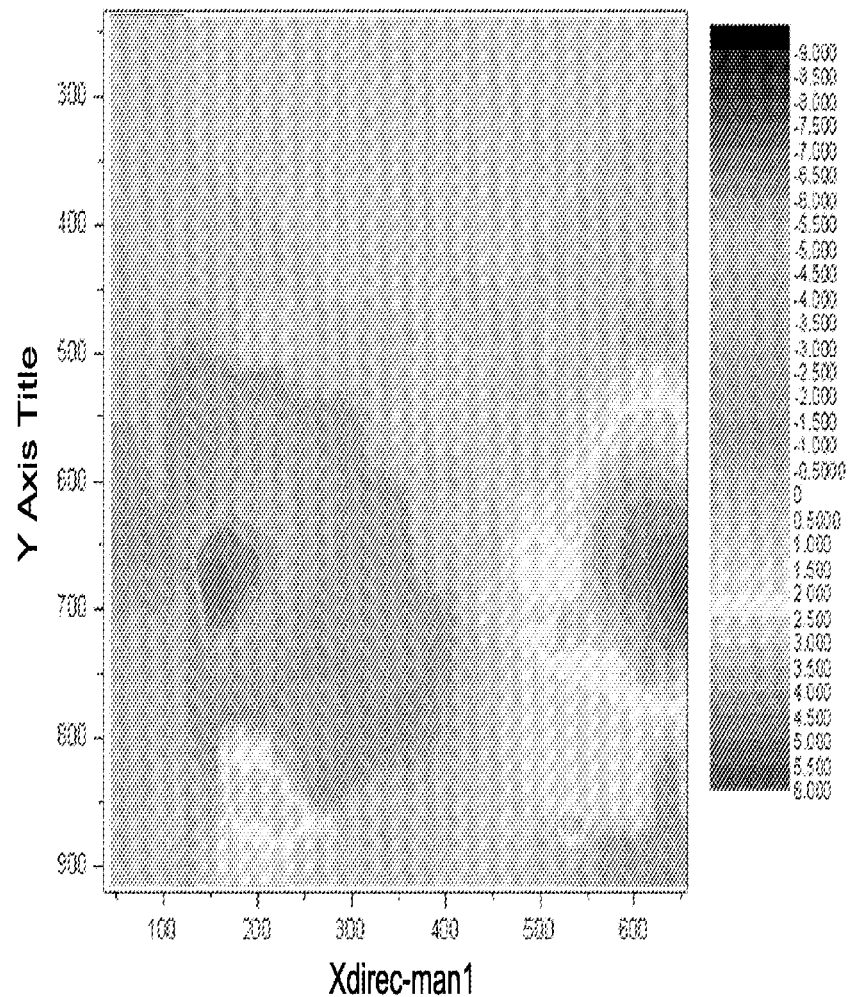
FIG. 6(Cont.)

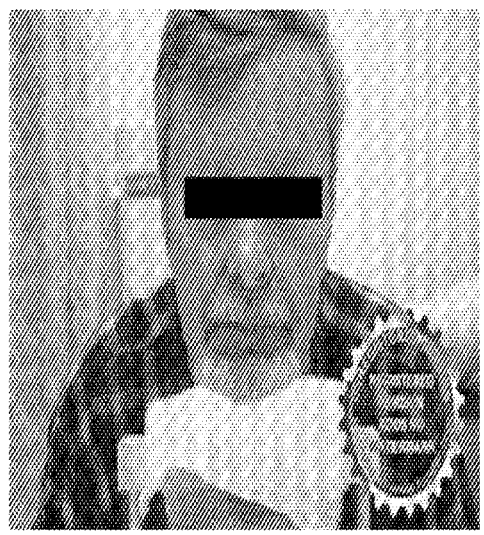
Subject 2: Post op(2005)
Neuroma: Left ; Size(mm): 6
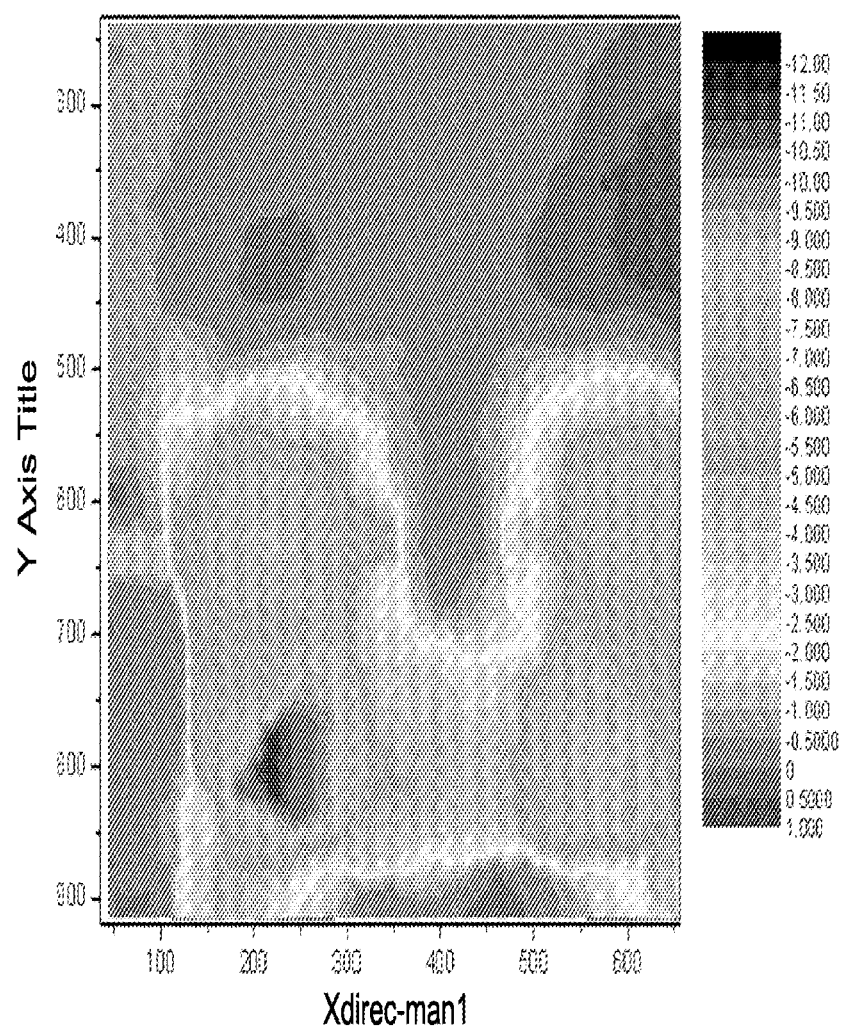
FIG. 6(Cont.)

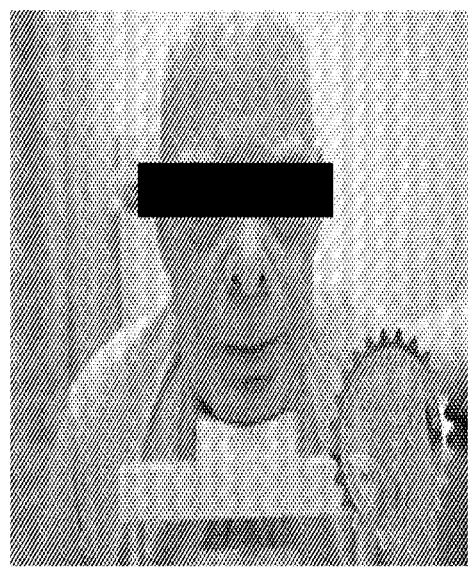 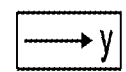 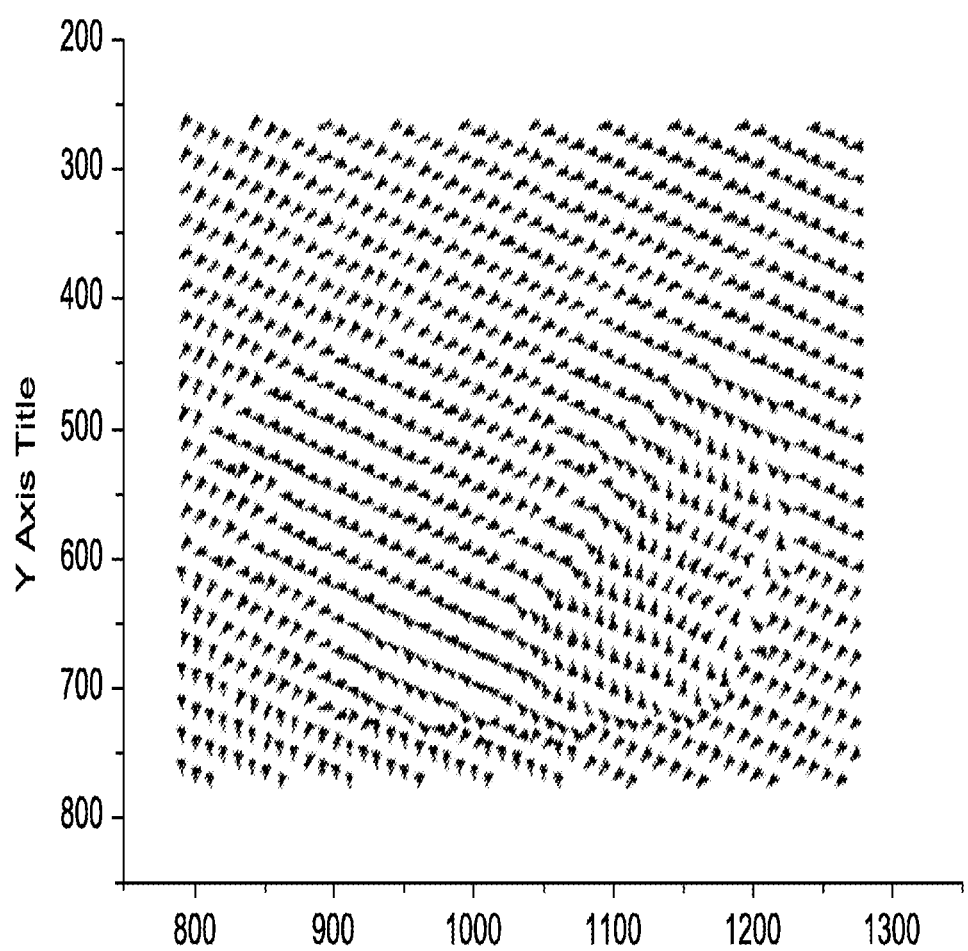
Vector Diagram-Subject 4
FIG. 7

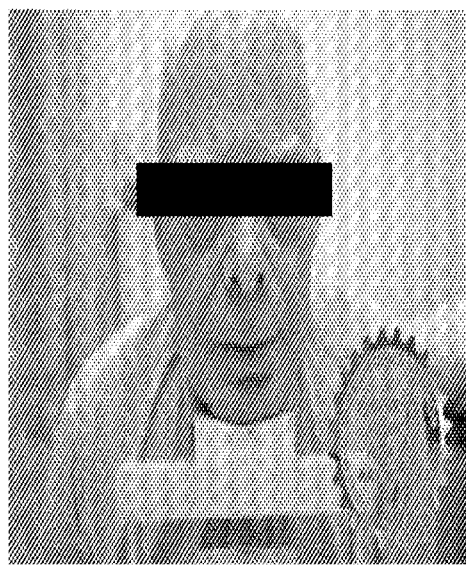
Subject 4: no surgery
Neuroma: Left ; Size(mm): 7
Motion Along: X-direction
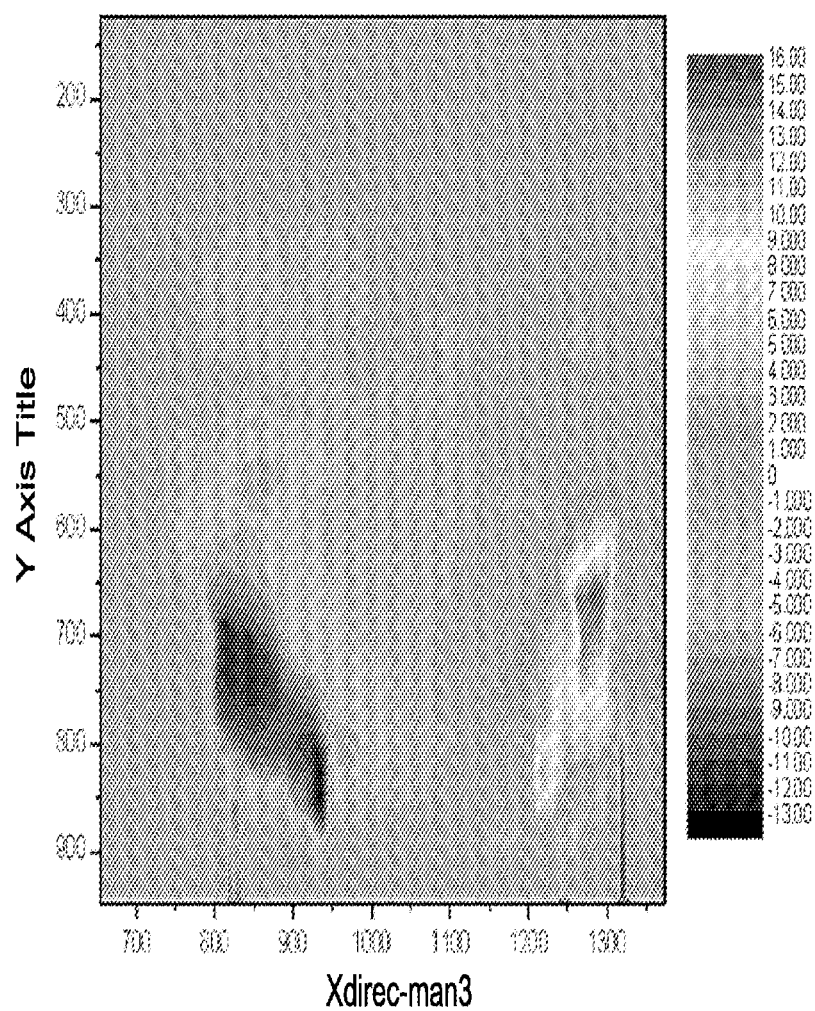
Xdirec-man3
FIG. 7(Cont.)

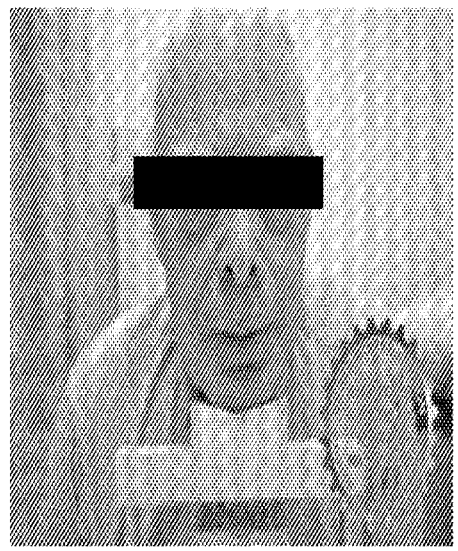
Subject 4: no surgery
Neuroma: Left ; Size(mm): 7
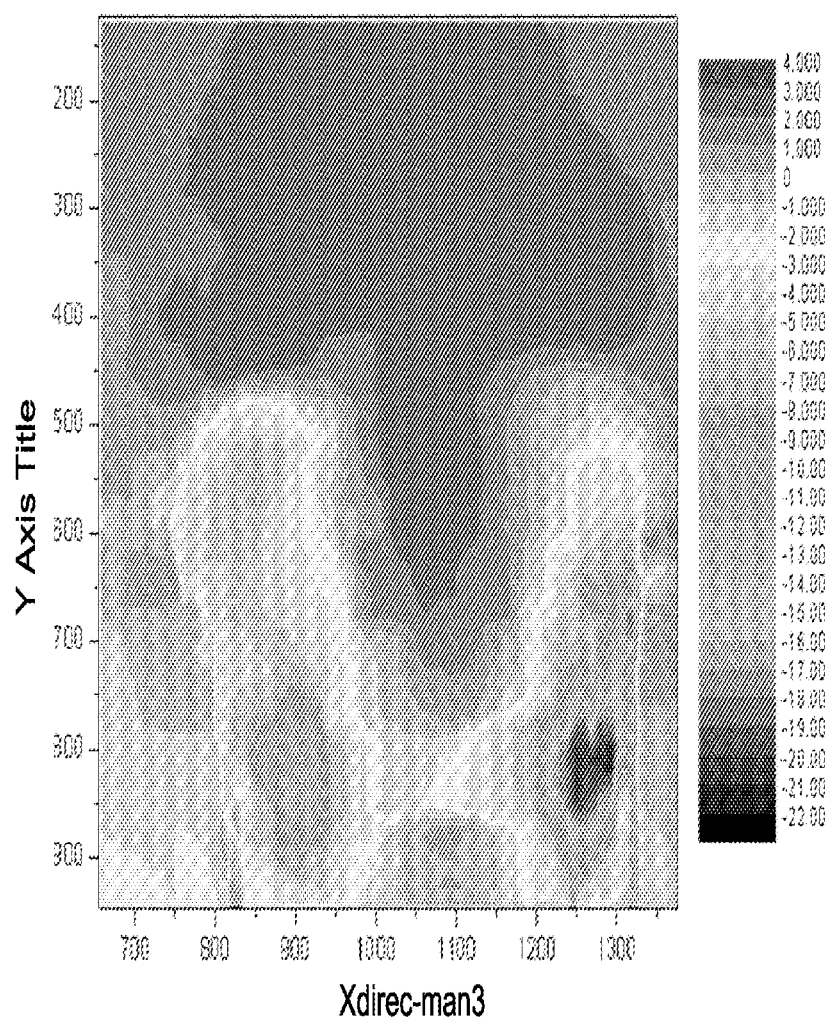
FIG. 7(Cont.)

METHODS USEFUL IN OPTIMIZING THE TREATMENT OF NEUROPATHIES AND TARGETING TISSUES WITH COSMETIC BOTULINUM INJECTIONS

CROSS-REFERENCE TO RELATED APPLICATIONS

This application is a continuation of U.S. application Ser. No. 13/463,766, filed May 3, 2012, which claims the benefit of priority to U.S. Application No. 61/482,057, filed May 3, 2011. The contents of which are incorporated herein by reference herein in their entirety.

STATEMENT REGARDING FEDERALLY FUNDED RESEARCH

This invention was made with government support under grant number DMR0606387 awarded by the National Science Foundation. The government has certain rights in the invention.

FIELD OF THE INVENTION

The present invention relates to both cosmetic treatments and to more serious conditions, including neuropathies (e.g., those caused by an acoustic neuroma) and stroke. More specifically, the invention relates to methods of optimizing where cosmetic agents such as botulinum toxin are best applied (e.g., injected); to methods of determining when and where treatment, including surgical intervention, for neuropathies should be undertaken; and to methods of evaluating the extent to which a patient's condition is improving or declining (e.g., as a neuropathy develops or during or after a stroke).

BACKGROUND

Digital Image Speckle Correlation (DISC) analysis is a sensitive, non-invasive technique that calculates the magnitude and vector of muscle contraction through photographic analysis. This technique has been used in animal studies of skin dynamics (see, e.g., Guan et al., *Dermatol.* 208(2):112-119, 2004). In addition, the technique has been used to characterize the biomechanical properties of human skin and to assess the effects of aging. For example, U.S. Patent Application No. 2007/0125390 describes methods of evaluating structural changes in the skin due to exogenous or endogenous factors. More specifically, U.S. Patent Application No. 2009/0022665 describes methods employing DISC analysis for evaluating immediate effect skin-molding agents, which are topically applied agents that cause a measurable, quantifiable change and/or reaction in the skin. Images are obtained before and after applying such agents in order to evaluate the skin's reaction and thereby determine the desirability of the agent. As noted therein, the methods provide for evaluating the skin's response to cosmetic, dermatologic or medicinal treatment or to any other factor alleged to affect the skin.

SUMMARY

The present invention is based on our conception of methods for extending DISC to direct clinical application. The methods are based on following the deformation of a set of speckles (e.g., a correlated set of speckles), whose density defines the spatial resolution (denser speckles providing greater spatial resolution). While conventional speckle material can be used, the pores intrinsic to the skin form an ideal set of features that can also be followed. Accordingly, any of the methods of the invention can employ extrinsic speckle material and/or intrinsic pores or other skin surface markers (e.g., the stubble of a beard). Instead of an applied force, which is used in traditional mechanical testing, or an invasive technique, the present methods can be carried out by analyzing natural motions, such as one or more of the following, to generate skin deformation: smiling (e.g., slight smiling), eye movement (e.g., blinking or looking in a defined direction), movement of the jaw, lips, or tongue (e.g., opening of the mouth), and movement of the forehead (e.g., raising one or both eyebrows and frowning). One then generates, based on the DISC or DISC-like analysis, a map of the deformation of the speckles or the cutaneous markers (e.g., a pore ensemble), which identifies the loci where stress is applied to the skin, the regions of dissipation of the elastic strain, and the specific combination of muscles involved in a given motion. This allows one to then assess variations in skin elasticity and to map the differences that exist among different regions of, for example, the face, including the area around the eye, the forehead, and the area around the mouth. The vector displacement of the skin generated by DISC or DISC-like analysis can further be used to calculate the magnitude and direction of muscle contraction.

As noted above, the present methods can be applied where non-cosmetic conditions or procedures are contemplated (e.g., an acoustic neuroma or following a stroke (whether pharmaceutically treated and/or treated with physical therapy). We applied DISC to see a change in nerve function of 12 patients suffering from acoustic neuroma. Another study was done to quantify the effects of botulinum toxin Type A (BOTOX®) on tension and contraction of treated muscle groups in six patients for a period of six months. Previously, many invasive techniques, which can be painful, have been used to see the effect of acoustic neuroma on nerve function. Similarly, for botulinum toxin injections, past treatment was based on subjective measures of aesthetic outcomes. While useful in determining patient satisfaction and self-image following treatment, these metrics fail to objectively quantify the direct effect of botulinum toxin on the facial musculature, nor do they allow us to predict a patient's response to treatment in a meaningful way. The present methods improve upon such outcomes. Despite several validated questionnaires, including the Facial Line Outcome (FLO-11) questionnaire and the Self-Perception of Age (SPA) measure, there is a lack of an objective measurement tool to determine the degree or duration of the toxin's effects (or of any other cosmetic procedure, such as the injection of a filler material to the lips, chin, cheekbones, or forehead). Our methods employ DISC as a sensitive non-invasive tool that derives corresponding displacement vectors through tracking geometric features on digital images before and after muscle deformation (e.g., before and after a patient is asked to assume a particular pose, such as smiling). By taking images (e.g., digitized images), DISC analysis can improve the current standard of care for cosmetic treatments in which an agent that alters the muscular function or form of the face is injected. We expect a similar improvement in the standard of care for neuropathies, including acoustic neuromas, as it can be difficult at present to track the rate of change and determine when to intervene and/or the success of an intervention. Moreover, the present methods can be adopted to analyze the extent of a stroke and/or a patient's recovery. They may be especially useful where the stroke is either mild (making an assessment of the impaired function difficult somewhat difficult to perceive) or major (as function can be so impaired, small degrees of improvement can be difficult to detect). In the case of cosmetic treatments, such as BOTOX® treatments, DISC analysis enhances clinical judgment by indicating where injections should be performed to produce optimal cosmetic results. Thus, the methods of the present invention are not limited to those (and can exclude those) in which the skin's response to cosmetic, dermatologic or medicinal treatment is evaluated following treatment. The present methods can be employed prior to treatment in order to inform the application of the treatment, for example, to optimize the treatment (e.g., by selecting a targeted area for treatment and/or determining the number and or size of an area or areas to be treated). The methods can also be applied both before and after the treatment; they are not merely evaluative. As indicated for neuromas, the present methods can help the treating physician or surgeon determine the effect of the neuroma on nerve function and treat the patient accordingly. The same is true in the event of stroke. Any of the methods of the invention can include a step of selecting or identifying a patient who will or who may benefit from treatment. As acoustic neuromas have been linked with the genetic disorder neurofibromatosis type 2 (NF2), the present methods focused on neuropathies can include a step of identifying a patient suffering from NF2. In addition, the methods can be employed over time to monitor the progress of a condition or the progress of recovery following nerve repair and/or muscular injection.

Although we tend to stress the use of DISC analysis, the invention is not limited to methods in which DISC, as strictly and currently understood, is applied. The present methods can be carried out using any technique that calculates the magnitude and direction (vector) of muscle contraction in a sufficiently sensitive manner. While photographic analysis is inexpensive and convenient, other imaging techniques that allow muscle contraction to be analyzed by DISC or a DISC-like technique can also be used.

BRIEF DESCRIPTION OF THE DRAWINGS

FIG. 1 is an outline of the photographic process and analysis for patients who wish to undergo a cosmetic procedure (e.g., BOTOX® injections) and patients with an acoustic neuroma.

FIG. 5 also includes a bar graph plotting the average degree of deformation over time.

FIG. 6 includes a photograph of a patient diagnosed as having an acoustic neuroma. This patient has already undergone surgical treatment, and the data shown in the contour and color maps are used to assess the degree of asymmetry of muscular activity (the color map on the left depicts motion along the X axis and the color map on the right depicts motion along the Y axis).

FIG. 7 includes a photograph of a patient diagnosed as having an acoustic neuroma. This patient has not undergone surgical treatment, and greater asymmetry in muscular ability relative to the treated patient assessed in FIG. 6 is evident in the contour and color maps generated from photographs using DISC analysis.

DETAILED DESCRIPTION

Figure 2:
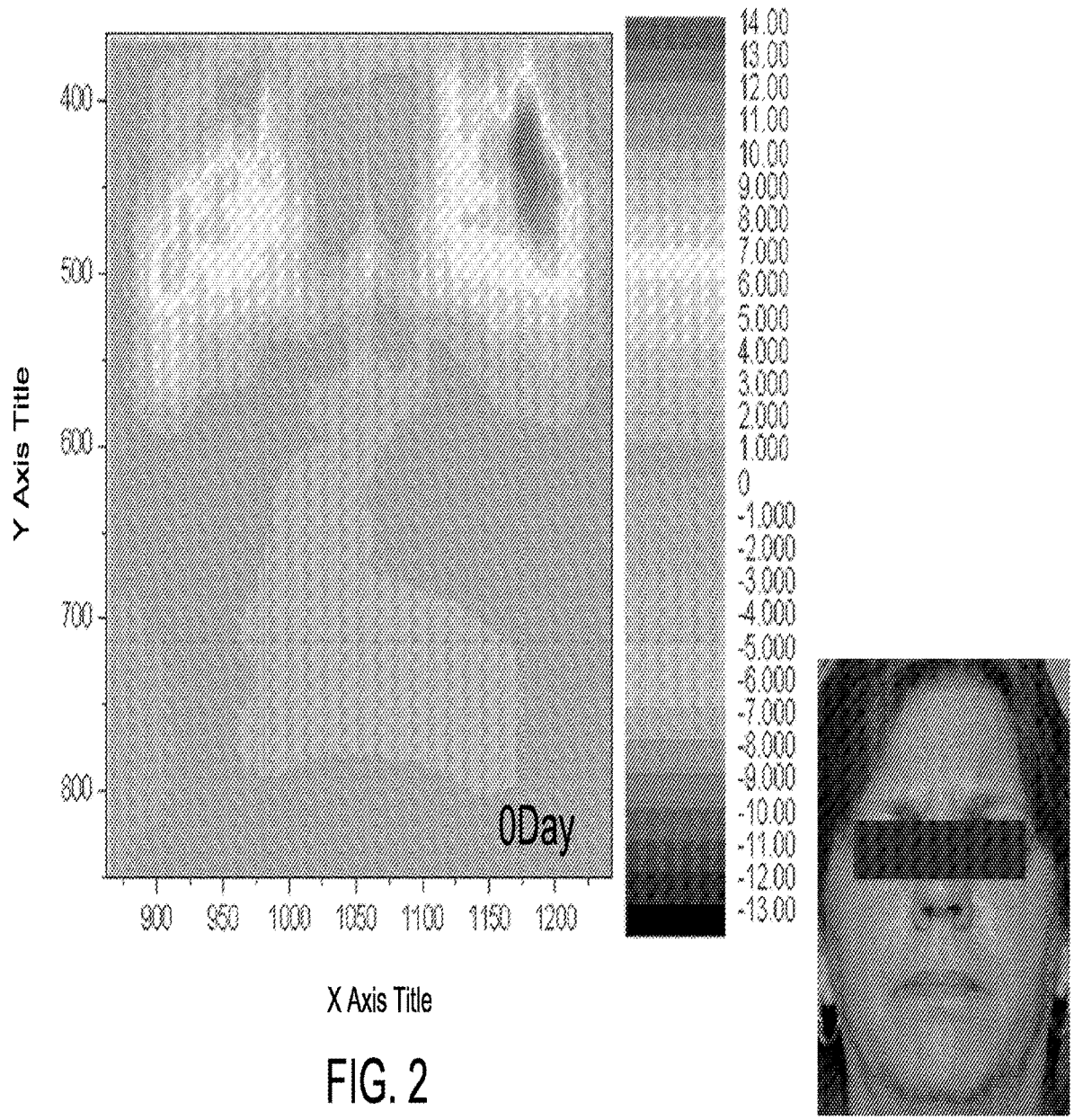
FIG. 2 includes a series of color maps produced by DISC analysis, a bar graph summarizing the data, and a representative photograph of a patient. Although the data in the color maps is much easier to discern from color photographs, one can see, even from the black and white copies shown here, the evidence of muscle contraction at "0 Day" when the patient is frowning (prior to BOTOX® injection), the lack of contraction due to muscle paralysis at "Week 1" and "Week 2", and the gradual return of muscle contraction over the subsequent periods of time when the patient frowns.
Figure 2:
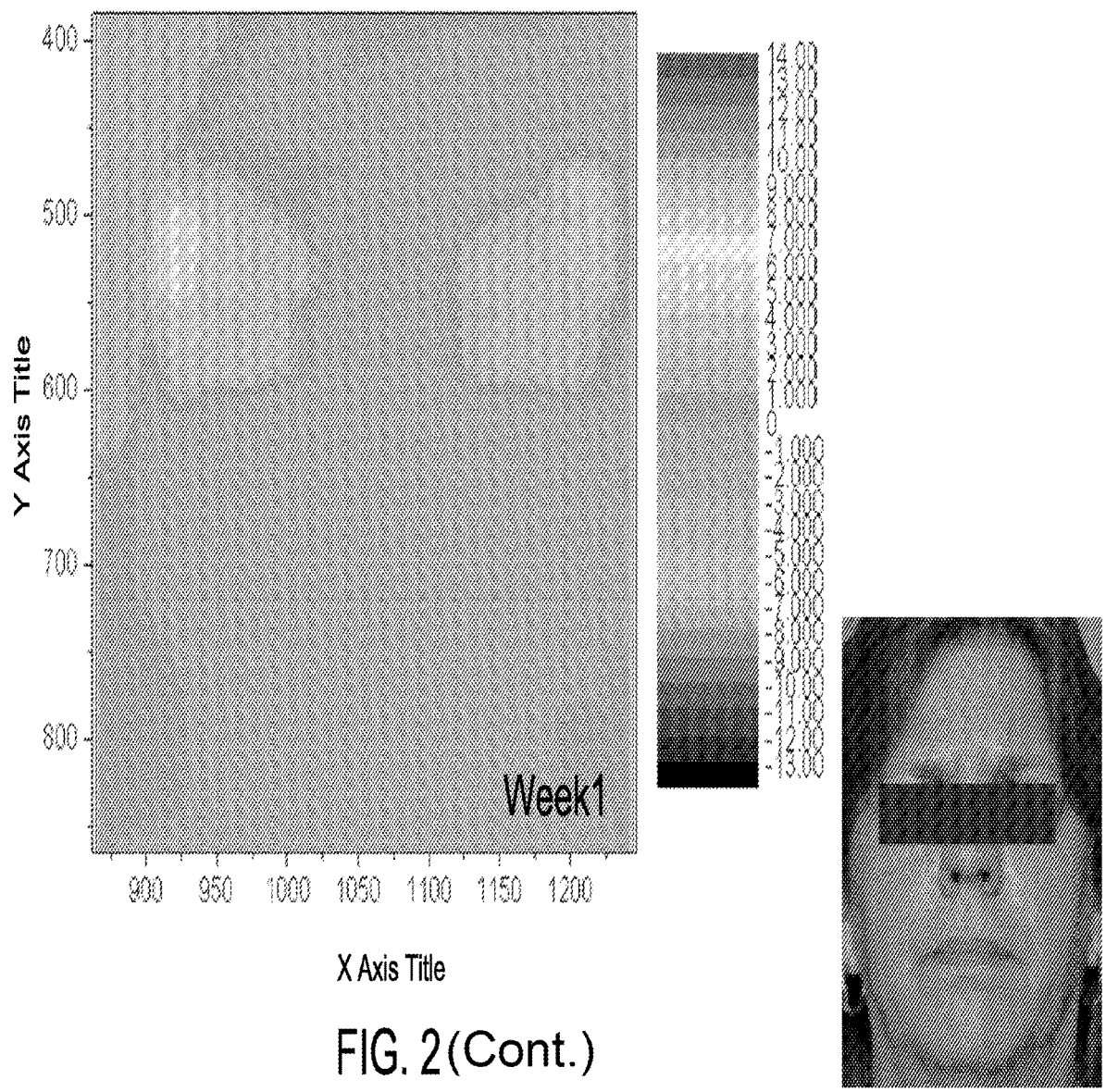
Figure 2:
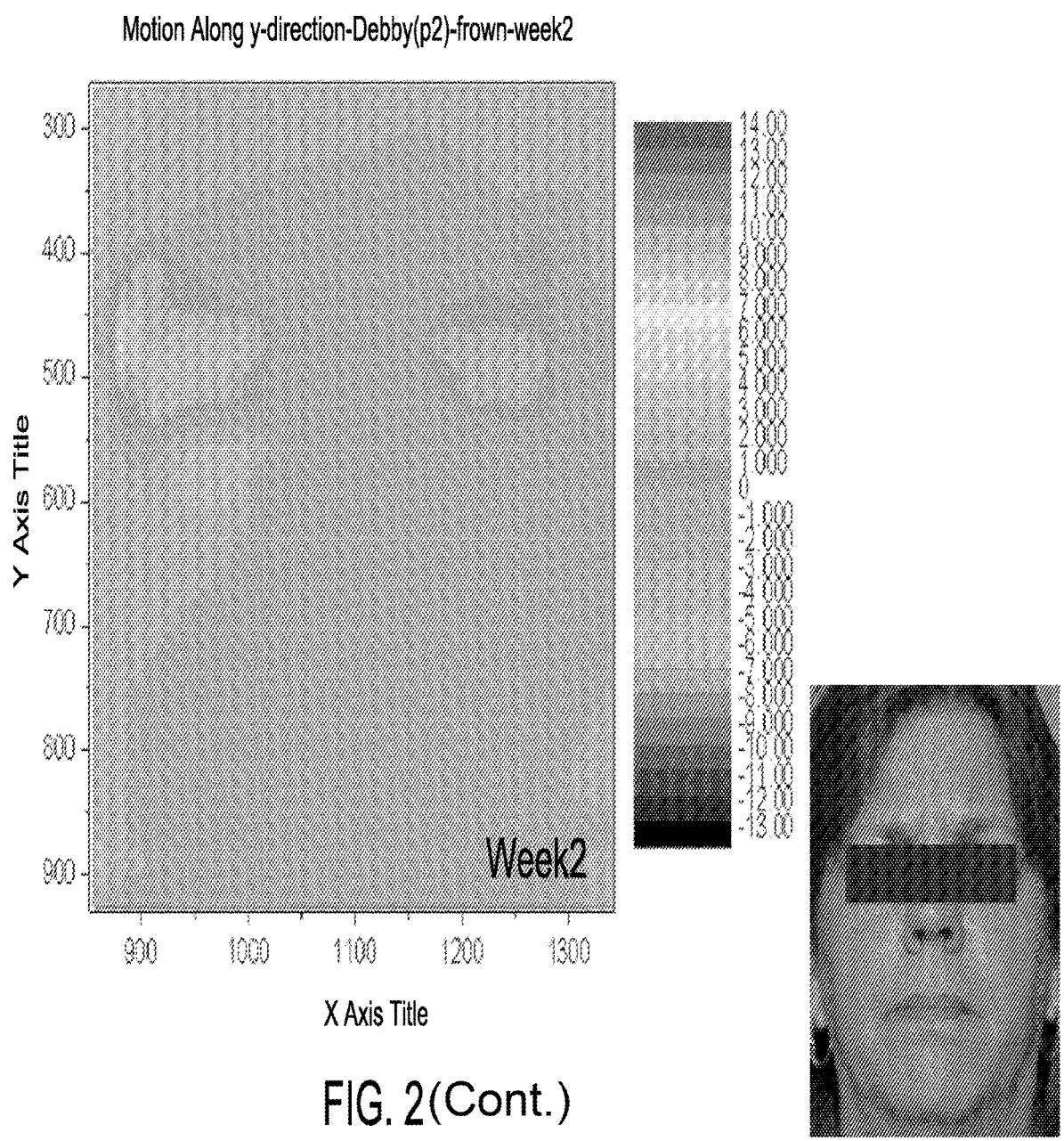
Figure 2:
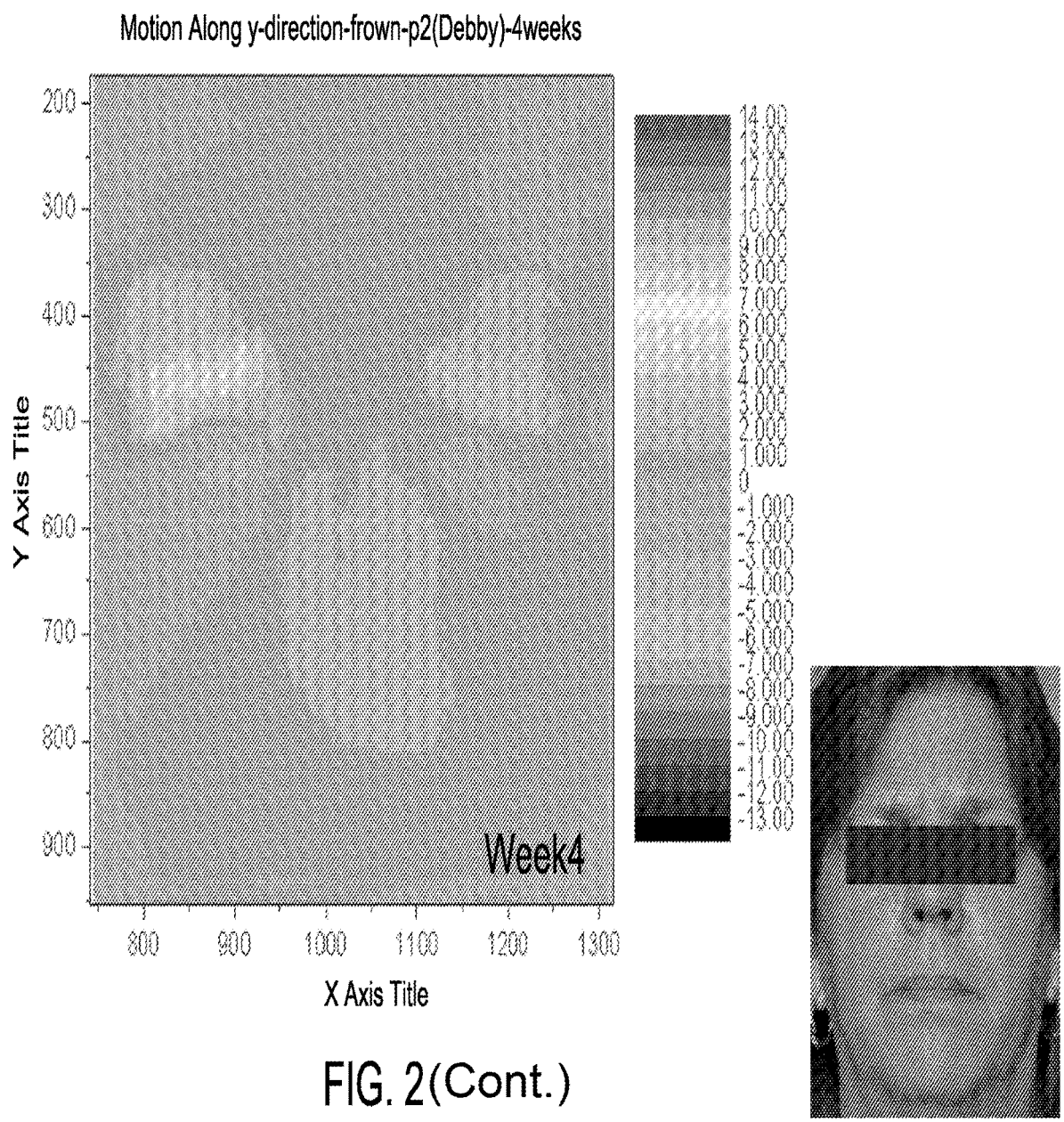
Figure 2:
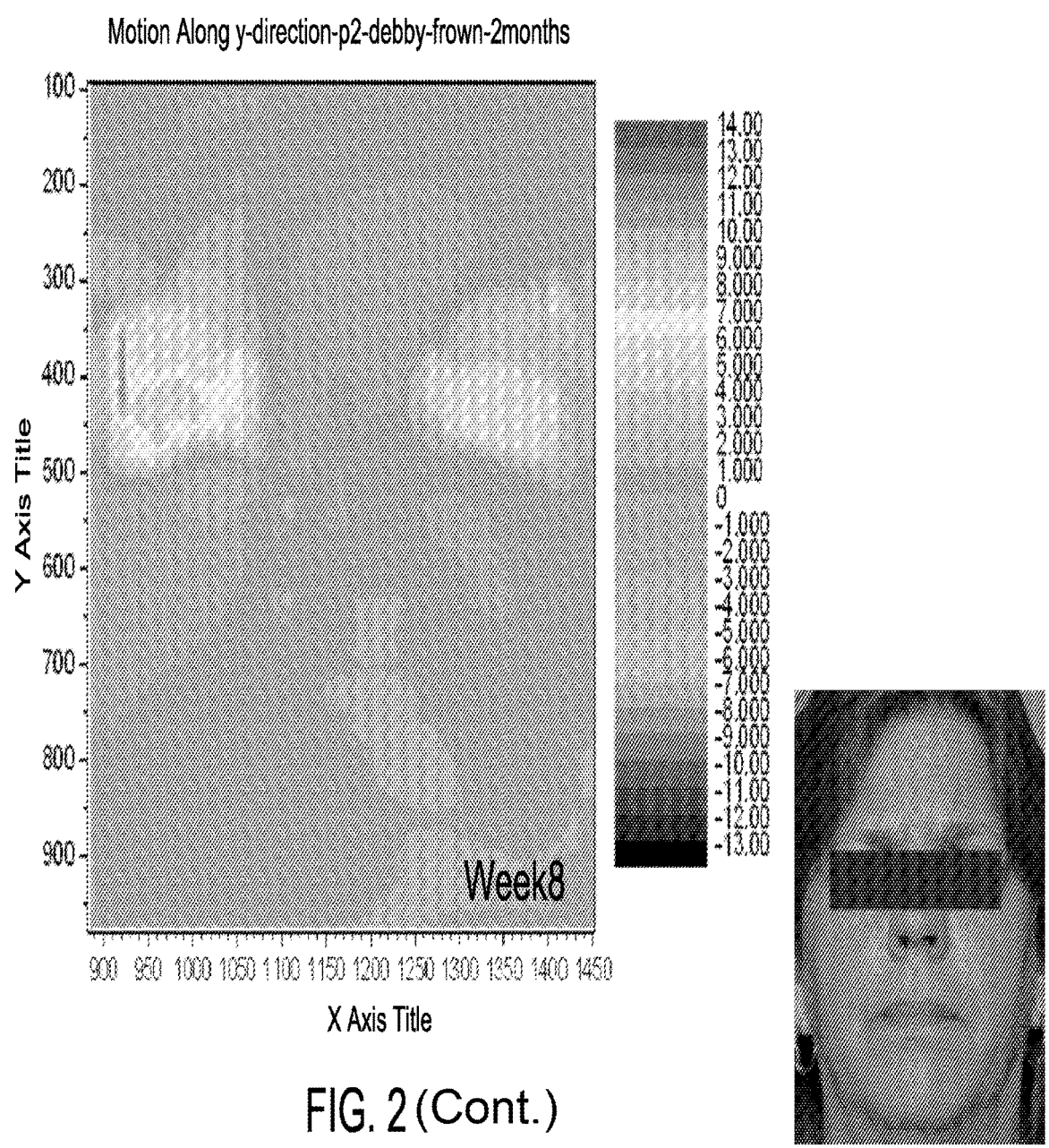
Figure 2:
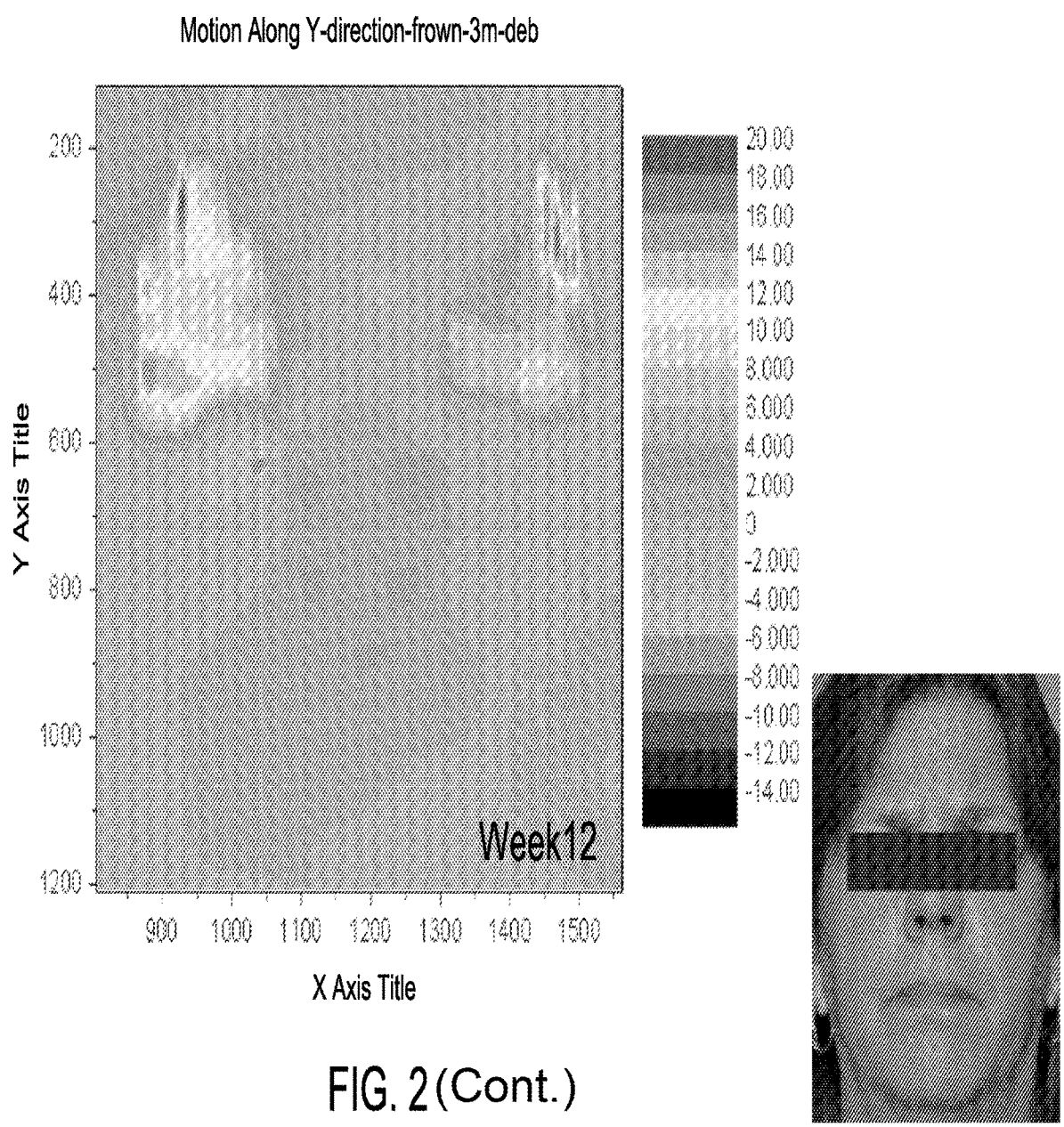
Figure 2:
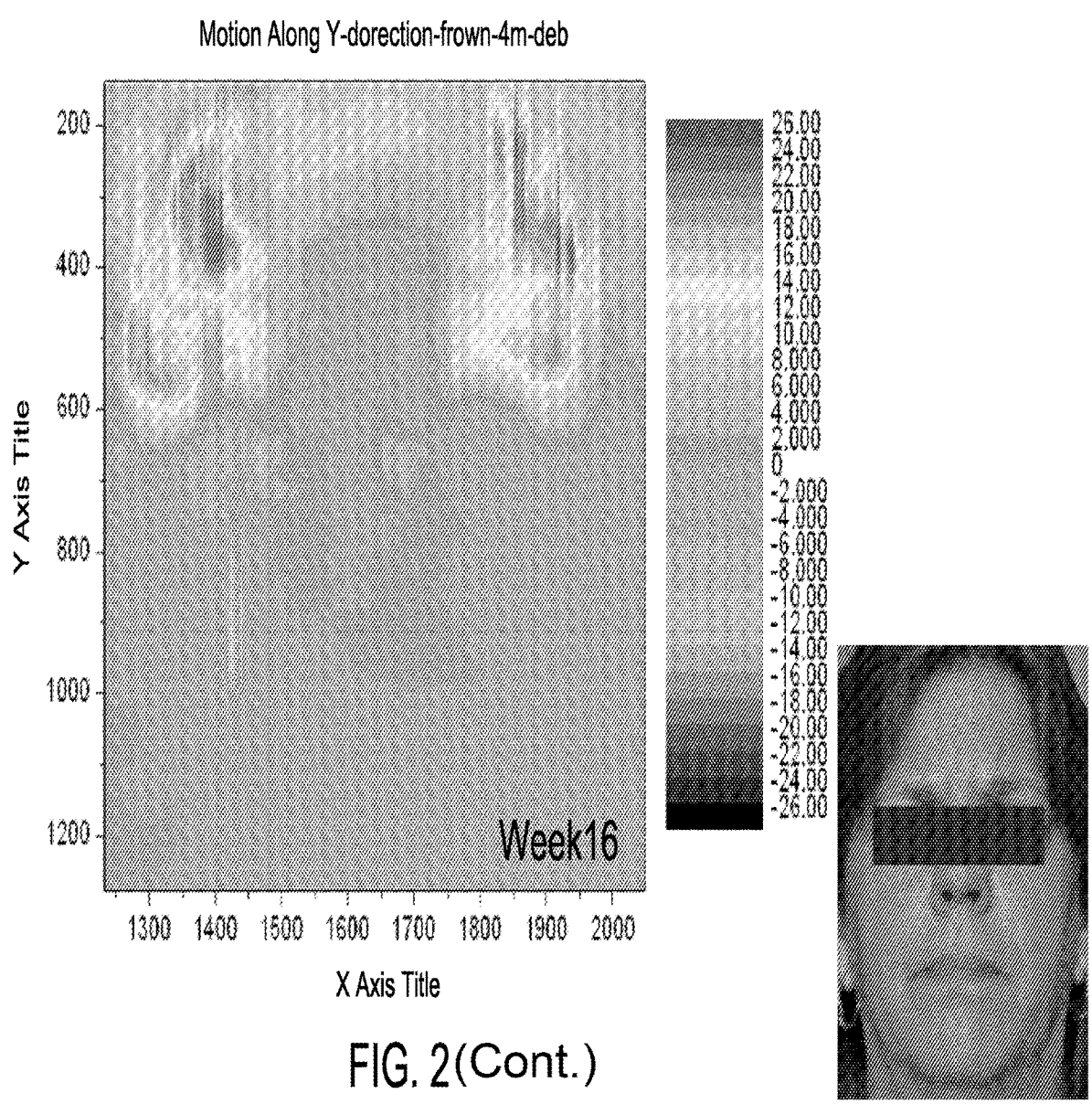
Figure 2:
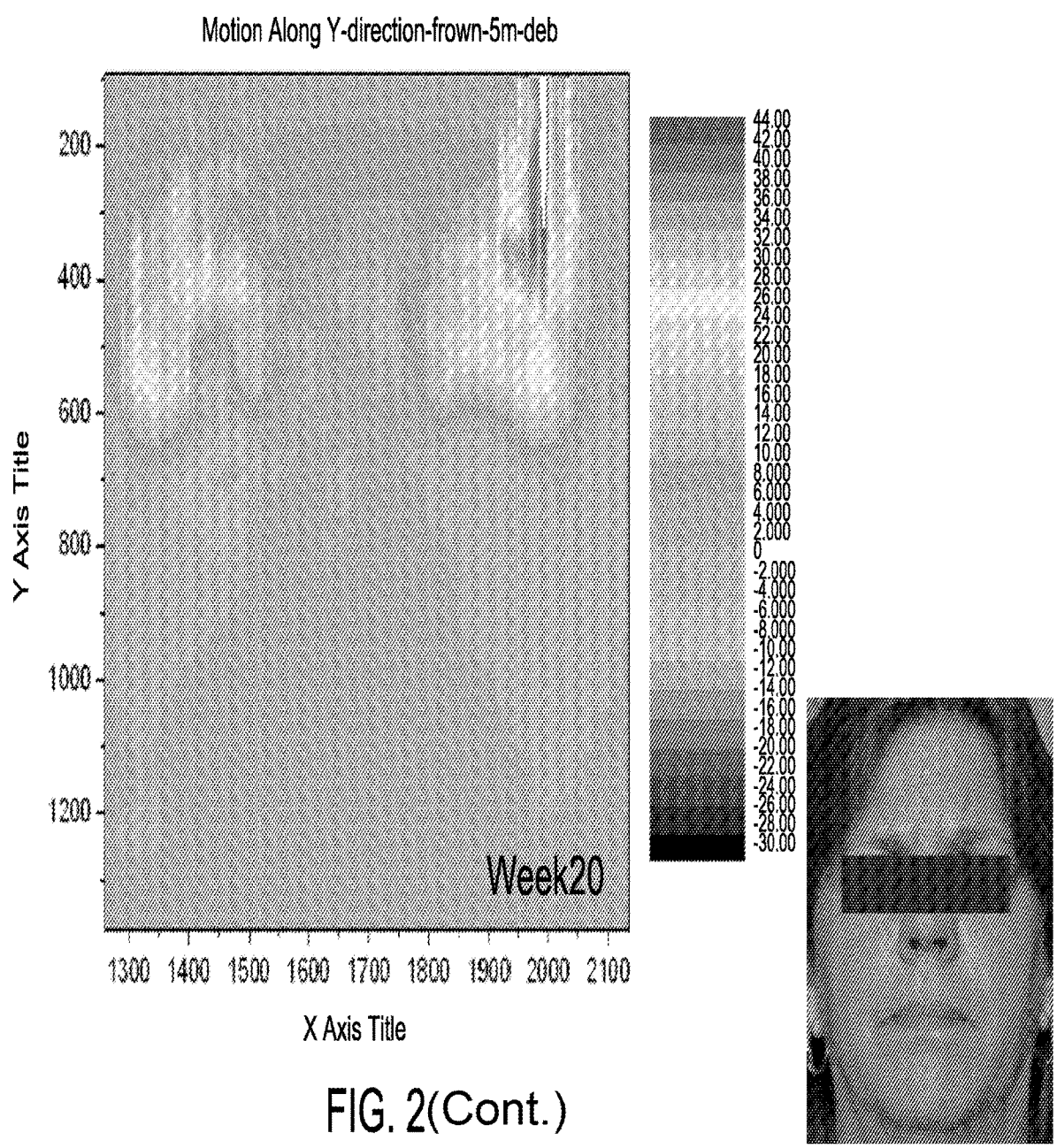
Figure 2:
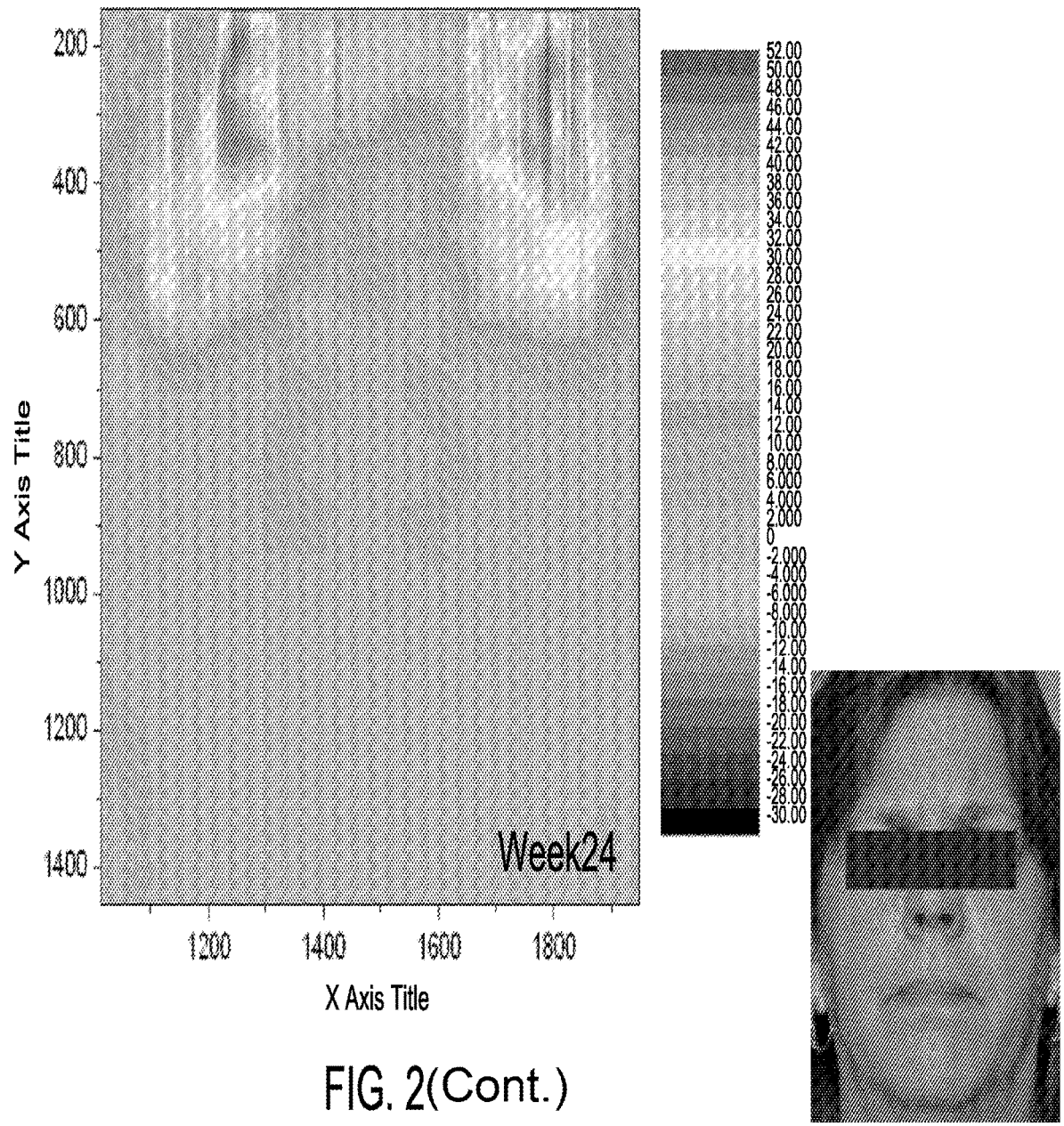

The present methods are based, in part, on our recognition that DISC analysis can be used to monitor enervation of muscles (e.g., facial muscles) and to monitor skin mechanics and the stress or tension on the skin from underlying muscles (e.g., facial muscles). Compared to previously known procedures for monitoring a patient (e.g., over time, either before or after a treatment regimen has been instituted), DISC is likely to be both less expensive and easier. We expect it will also provide detailed information about muscle paralysis, tension, and contraction. Moreover, in the context of BOTOX® injections, we expect DISC to be useful in quantifying the initial paralysis of each treated muscle group (e.g., in the forehead, glabellar complex, and around the eyes) and in revealing differences in the response to treatment among the muscle groups, including the rate of return-of-function over time. Another expected advantage of the present methods is that, while the data obtained may reveal certain general constants, they also provide highly individualized or "personal" treatments. In the context of BOTOX® injections, DISC analysis enhances or supplements visual, clinical judgment by providing indicators of where the BOTOX® injections should be made to produce optimal cosmetic results.

The outline provided as FIG. 1 shows that patients who are contemplating BOTOX® injections would be photographed at least twice; once with their faces at rest and once while making a small movement (e.g., raising their eyebrows to generate muscle contraction in the forehead; frowning to contract the muscles in the glabellar complex, between the eyebrows; or blinking to generate muscle contraction in the area where "crow's feet" typically develop). The paired images (e.g., photographs; resting and non-resting) can be taken over time (e.g., prior to BOTOX® injection, at about 1 week, 2 weeks, 4 weeks, and monthly for up to about six months following the injection(s)). The digital photographs obtained can be analyzed using DISC analysis, and facial muscle contraction can be quantified and compared to baseline. If desired, the quantitative analysis can be corroborated with FLO-11 ®, SPA®, Measure, and SGA (physician and patient) scores.

The outline provided as FIG. 1 also shows that patients who have been diagnosed with an acoustic neuroma can similarly be photographed with their faces at rest and while making a movement (e.g., a small movement). The photographs can be taken at points in time (e.g., approximately weekly, monthly, or quarterly) to monitor the progression of the neuroma prior to treatment or at points in time (e.g., approximately weekly, monthly, or quarterly) to monitor the patient's progress or recovery after treatment (e.g., surgical intervention for the neuroma). DISC analysis is used to analyze the digital photographs.

A suitable DISC system is described in U.S. Application Publication No. 2007/0125390, and that system and systems like it can be used in the present methods. Thus, as described in the application just mentioned, the system can include a camera for capturing digital images (preferably providing a minimum of four mega pixel resolution). This resolution is sufficient to resolve the pores of human skin, which can be the cutaneous points being tracked in the methods of the present invention. While virtually any feature in the image field may be used to track between images, successful DISC-type techniques depend on a plurality of features to track. As noted above, in humans, skin pores fulfill this requirement. Some useful cameras (as previously described in the application just mentioned) are Canon EOS Rebel Digital camera (6.3 mega pixel resolution), the Toshiba DK-120F CCD camera, the five-mega pixel Canon D60 or Canon Powershot ProI. Data collected by the camera can be pre-processed by a frame grabber, such as PIXCI® from EPIX®, and the digitized information is downloaded to a computer for numerical analysis. Other research groups have developed their own software on the DISC technique to suit their own needs; thus, there is room for customization and such modifications and adaptations are within the skill of one of ordinary skill in the art. Persons of ordinary skill in the art are capable of developing such software without undue burden. Furthermore, there are also commercially available software applications, one being VIC-2D from Correlated Solutions Inc. (West Colombia, S.C.), with an advertised displacement accuracy of better than one one-hundredth of a pixel. Another supplier of digital image correlation systems and software is Optical Metrology Innovations (Cork, Ireland; as noted in the aforementioned U.S. application).

In one embodiment, the methods comprise capturing two or more images of the subject. A procedure with just two images is described, and easily extended to more than two images. A first image of a surface (i.e. a portion of skin) can be made when the skin and underlying muscles are at rest and a second image of the surface can be made when the patient has generated some movement (e.g., by performing a grin or slight smile; in the event of a neurological impairment, the movement will obviously vary depending on the patient's ability to achieve the desired muscle control). To facilitate the methods, the area of the patient's body being imaged can be partially immobilized. For example, where the area of study is on the face, a chin rest or other device may be used to help hold a subject's head still. Useful devices of this type are available from Canfield Scientific. It is also preferable that the camera (or other image capture device) be held still during use.

As described in U.S. Application Publication No. 2007/0125390, software, such as Photoshop from Adobe®, can be employed once an image has been obtained. For example, such software can be used to impose on the images a boundary of the area to be studied and a reference coordinate system. The software can also be used for obtaining a rough estimate of pore displacement. As described in the aforementioned application, the boundaries can be somewhat arbitrary and may be chosen to define a domain large enough for analyzing several areas of the skin. More sophisticated image analysis software is commercially available. For example, products sold under the OriginLab® label are able to analyze DISC-type digital image data to calculate values for a host of mechanical properties of the material under investigation. The image analysis software determines the coordinates of each pore in the displacement field relative to the reference coordinate system, for the before and after image. From this data, correlations are established between the pores in the before and after images and a field of displacement vectors, as discussed above, may be generated. Each displacement vector represents the movement of one pore from its initial to final location. Each pore vector in the field of displacement vectors is resolved into its vertical and horizontal projections, from which vertical and/or horizontal projection maps may be produced. In the projection maps, the horizontal and vertical axes convey the coordinates of any position in the field of study. Areas of constant displacement are color coded in these figures. By measuring the displacement of features (pores) at the boundary of the image area, it is, in principle, straightforward to calculate the change in size of the image area. The change in size along the vertical and horizontal directions may be separately calculated, or a total deformation of the image region may be calculated. These may be expressed as percent change in size or strain, induced in the bounded area.

Alternatively, sufficiently sophisticated digital analysis software is available (i.e. OriginLab®) that can analyze the entire displacement field and directly calculate strain at any position and average strain over the field.

Accordingly, in one aspect the invention features methods, which we may also refer to as techniques (e.g., a non-invasive technique) for assessing nerve function in the skin. The methods can include the step of obtaining an image of the patient (e.g., photographing a patient) suspected of having compromised nerve function. The images (e.g., photographs) can be taken of one or more areas of the patient's skin while the patient is at rest and then taken again while the patient is performing an action. The images (e.g., photographs) are then subjected to DISC or DISC-like analysis. The patient can be suspected of having an acoustic neuroma, and the one or more areas of the patient's skin that are imaged can be areas of skin on the patient's face or neck. The skin can also be located on one or more of the chest, back, arm, leg, hand or foot. In the "non-rest" or active position, the patient may have been instructed to perform one or more of the following movements: moving the jaw, lips, or tongue; moving the eyes; or moving the forehead. The DISC or DISC-like analysis can be performed on two or more occasions in time in order to assess the stability or instability of the nerve function. The DISC analysis per se can include a step of quantifying the strength and/or qualifying the direction of the effect produced when the patient is performing an action relative to the patient at rest. The DISC analysis can also include the step of examining one or more vector displacement maps of skin markers (e.g., pores). The DISC analysis can further include the step of identifying the principle axis of strain in the vector displacement maps.

In another aspect, the invention features methods or techniques (e.g., non-invasive techniques) for determining where a cosmetic agent that causes muscle paralysis should be injected. These methods also include a step of imaging (e.g., photographing) a patient. However, these patients are those who wish to be treated with a cosmetic agent. The images (e.g., photographs) are taken of one or more areas of the patient's skin while the patient is at rest and again while the patient is performing an action. The images (e.g., photographs) are then subjected to DISC or DISC-like analysis. These methods can further include a step of generating a vector diagram based on the DISC analysis that indicates the locus of large stress on the skin from muscular tension and a step of injecting the cosmetic agent at the locus of large stress. The areas of the patient's skin one would image can include the skin of the face or neck, and the patient may have been instructed to perform one or more of the following movements: moving the jaw, lips, or tongue; moving the eyes; or moving the forehead. The DISC analysis per se can include a step of quantifying the strength and/or qualifying the direction (magnitude and direction; vector) of the effect produced when the patient is performing an action relative to the patient at rest.

In another aspect, the invention features methods or techniques (e.g., non-invasive techniques) for assessing a patient's recovery from stroke. The methods can include the step of imaging (e.g., photographing) a patient who has had a stroke. The images (e.g., photographs) can be taken of one or more areas of the patient's skin covering an area of the body affected by the stroke. For example, an area of the body that is paralyzed to some extent. The images are obtained while the patient is at rest and again while the patient is attempting to move the area of the body affected by the stroke, and the images are then subjected to DISC or a DISC-like analysis. The one or more areas of the patient's skin can include skin of the face or neck, but may also be skin covering some or all of the chest, back, arms, legs, hands, or feet. The patient may be instructed to perform one or more of the following movements: moving the jaw, lips, or tongue; moving the eyes; moving the forehead; or tensing a muscle in the chest, back, arms, legs, hands, or feet. The DISC analysis can be performed on two or more occasions in time in order to assess the patient's ability to move the area of the body affected by the stroke as time passes. The DISC analysis per se can include quantifying the strength and/or qualifying the direction of the effect produced when the patient is performing an action (or attempting to perform an action) relative to the patient at rest. The DISC or DISC-like analysis can also include the step of examining one or more vector displacement maps of skin markers (e.g., pores).

In any of the methods of the invention, the steps can include either imaging (e.g., photographing) a patient or providing an image (e.g., a photograph) of a patient. In the event of a neurological impairment, the methods can be carried out while a patient is undergoing a treatment in order to help the physician assess the efficacy of the treatment.

EXAMPLES

Figure 3:
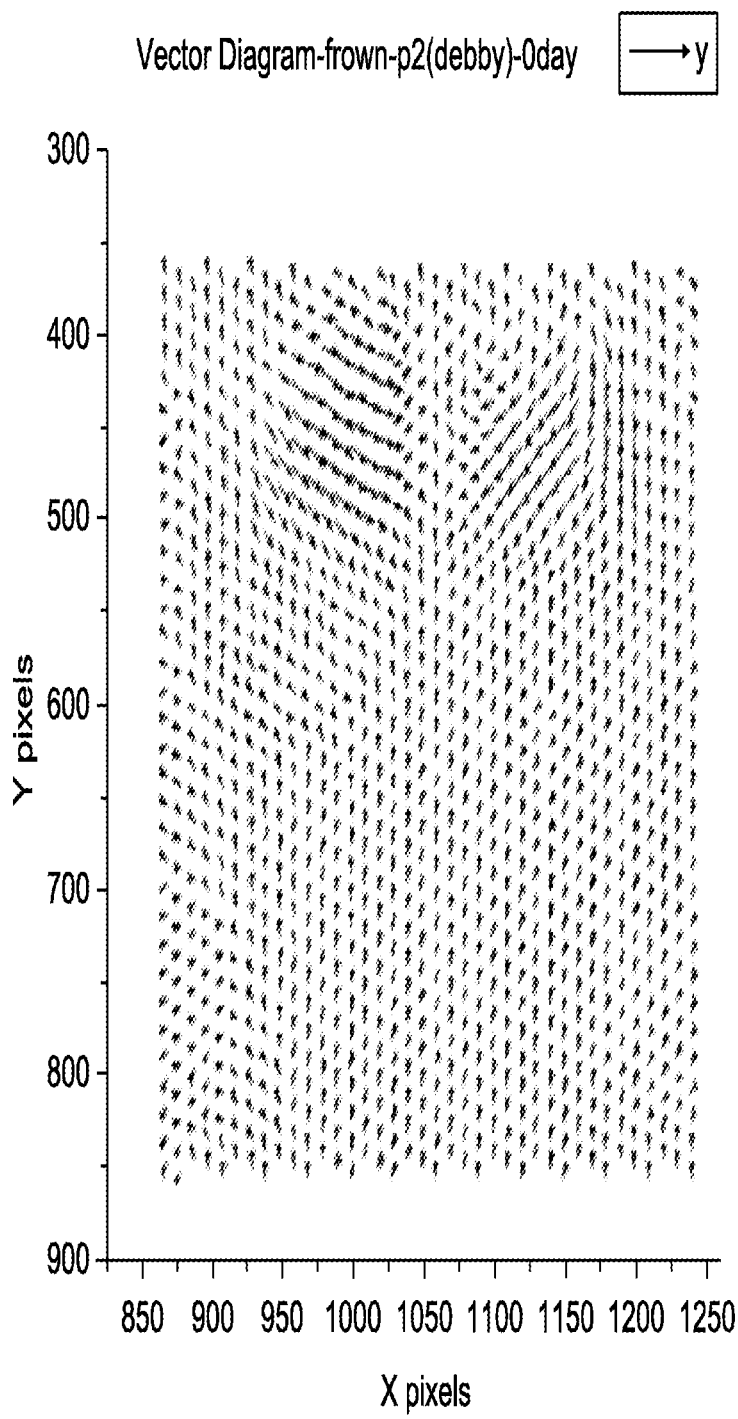
FIG. 3 is a series of contour maps produced by DISC analysis, with the length and direction of the arrows indicating the magnitude and direction of muscle tension generated in a patient who was photographed while frowning. The contour maps were generated at the times shown (i.e., at "0day" (upper left) and then at 1, 2, and 4 weeks after BOTOX® injection (moving from left to right across the top row of contour maps); photographs taken at later times, as labeled, are shown in the second and third rows).
Figure 3:
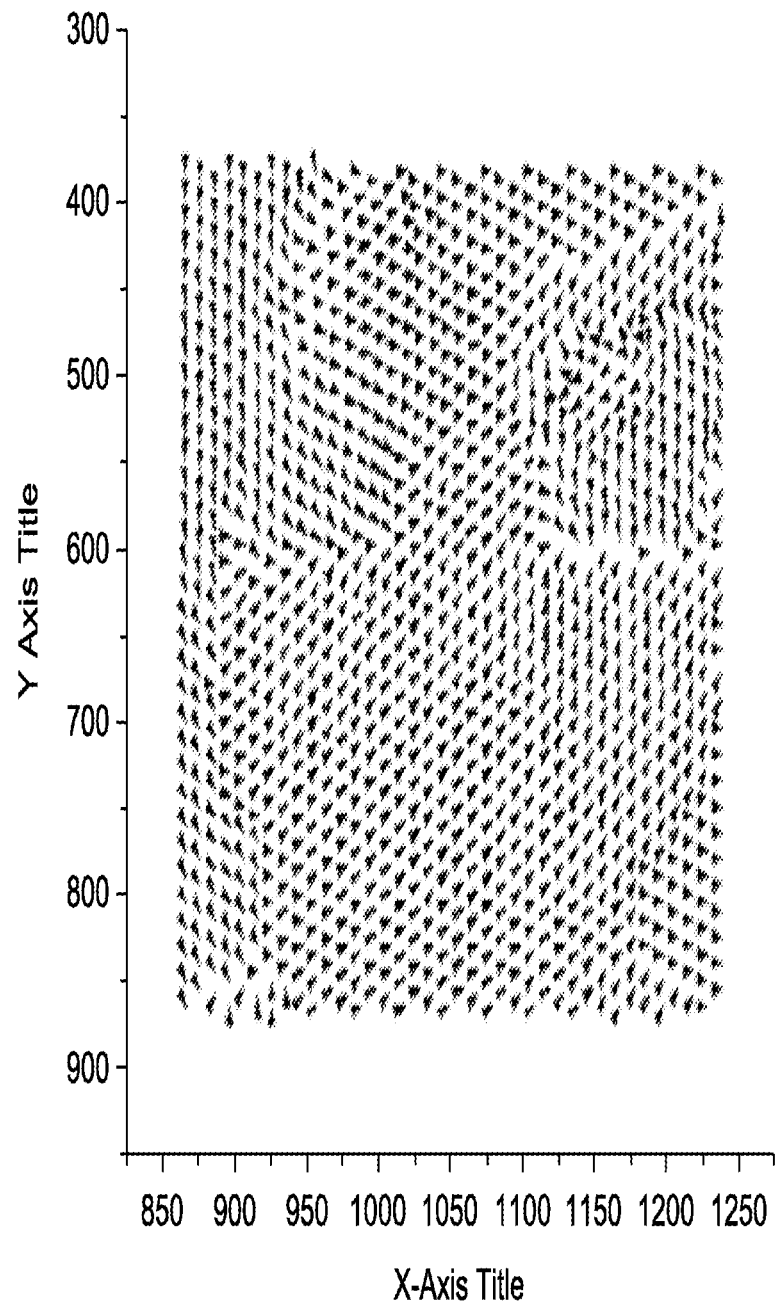
Figure 3:
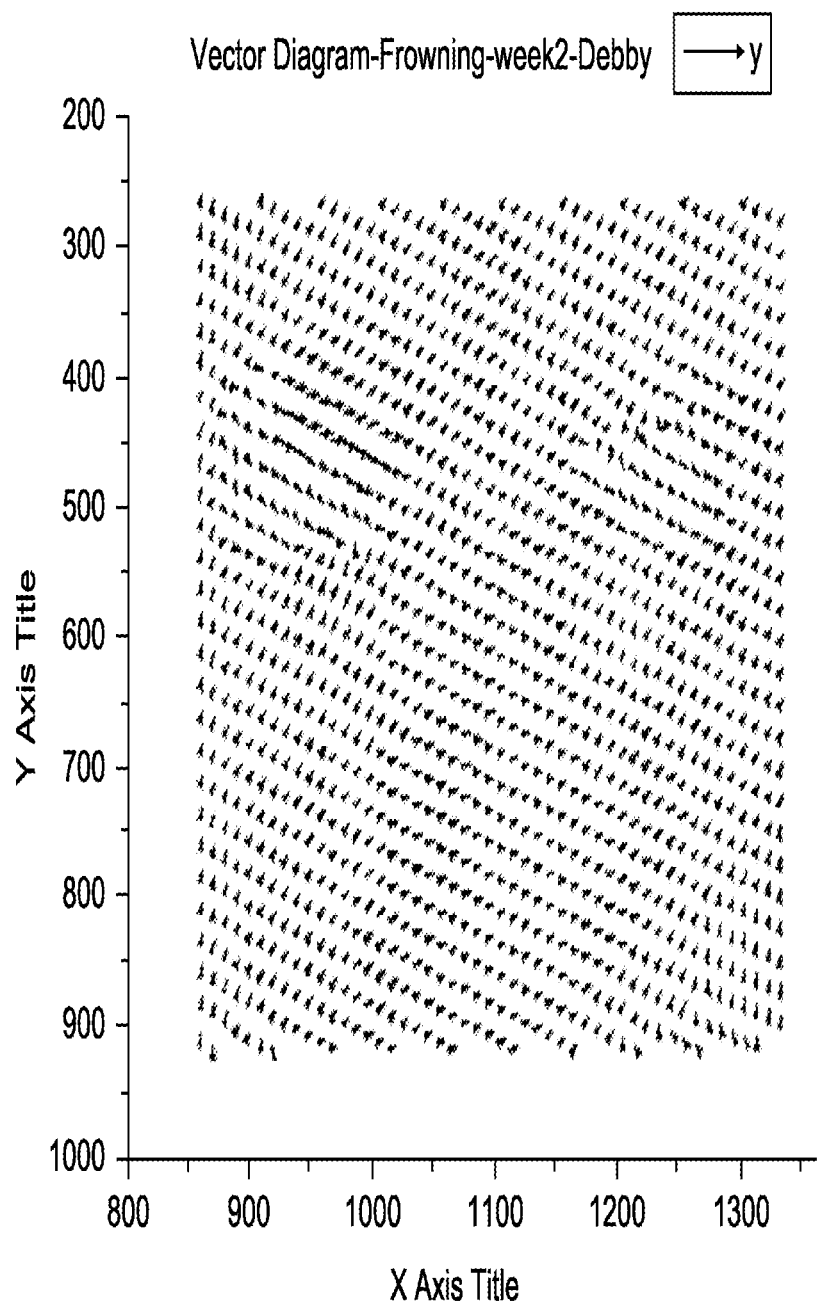
Figure 3:
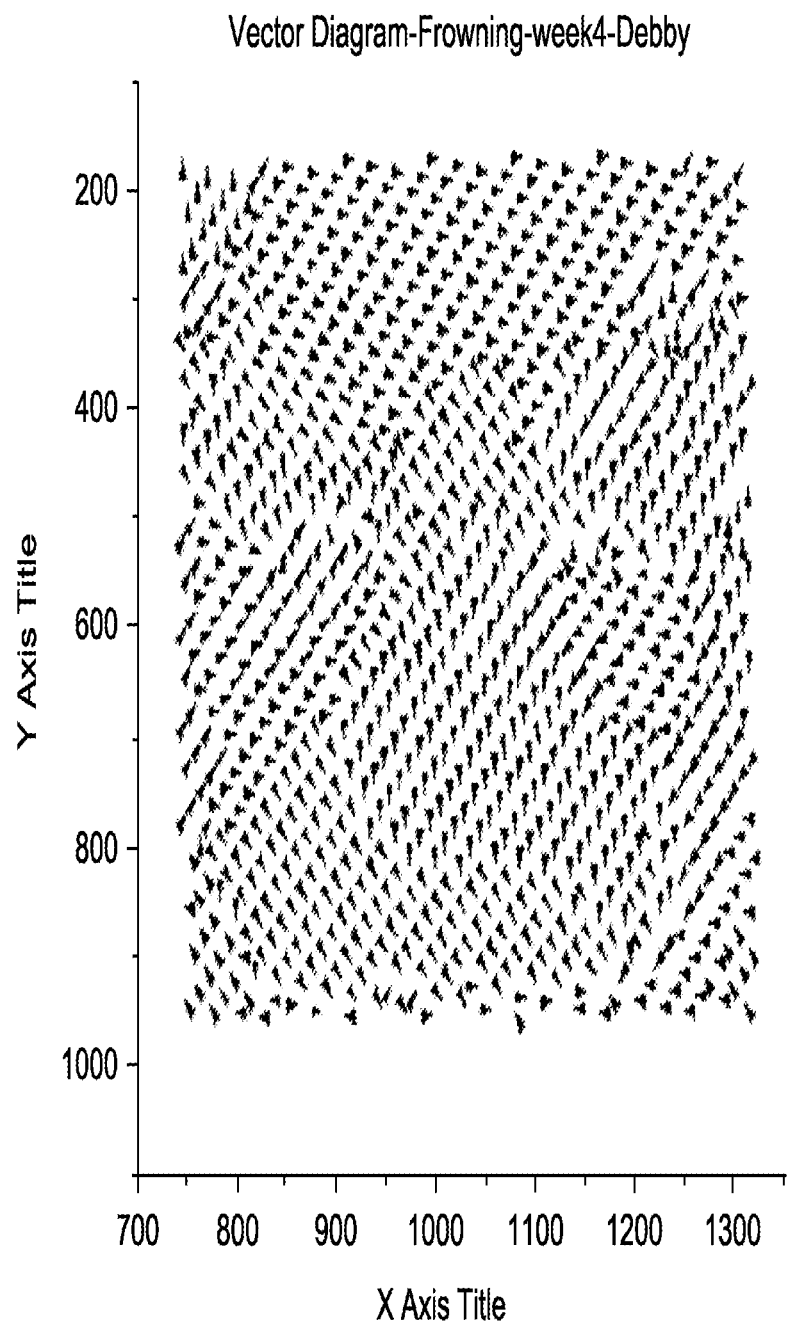
Figure 3:
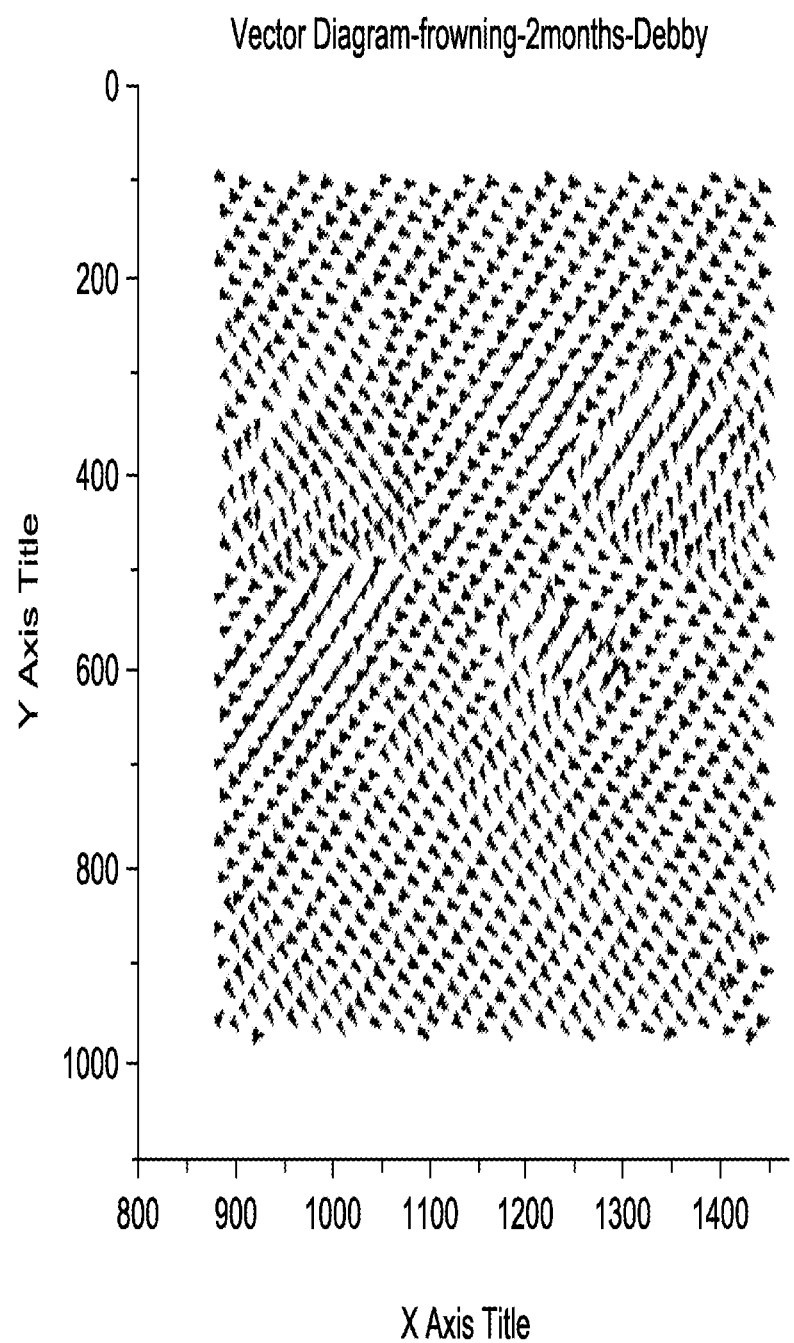
Figure 3:
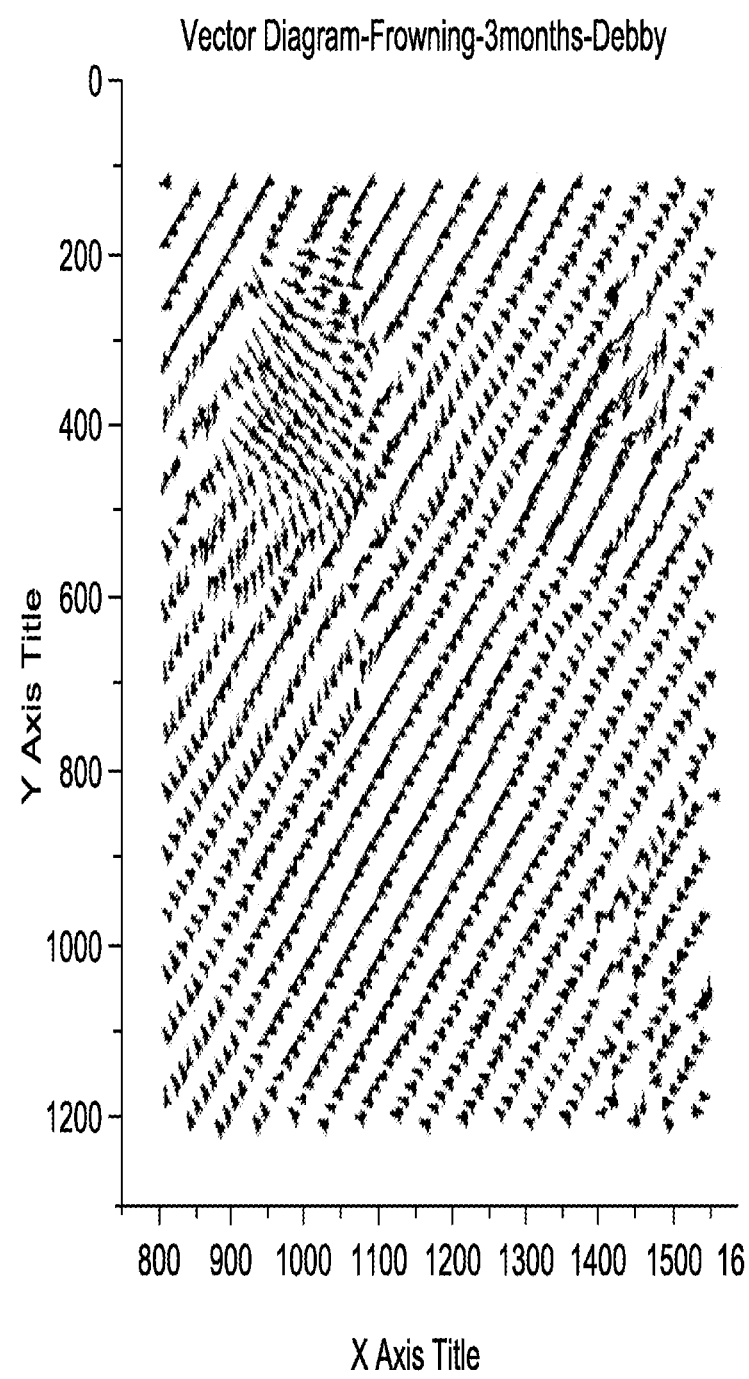
Figure 3:
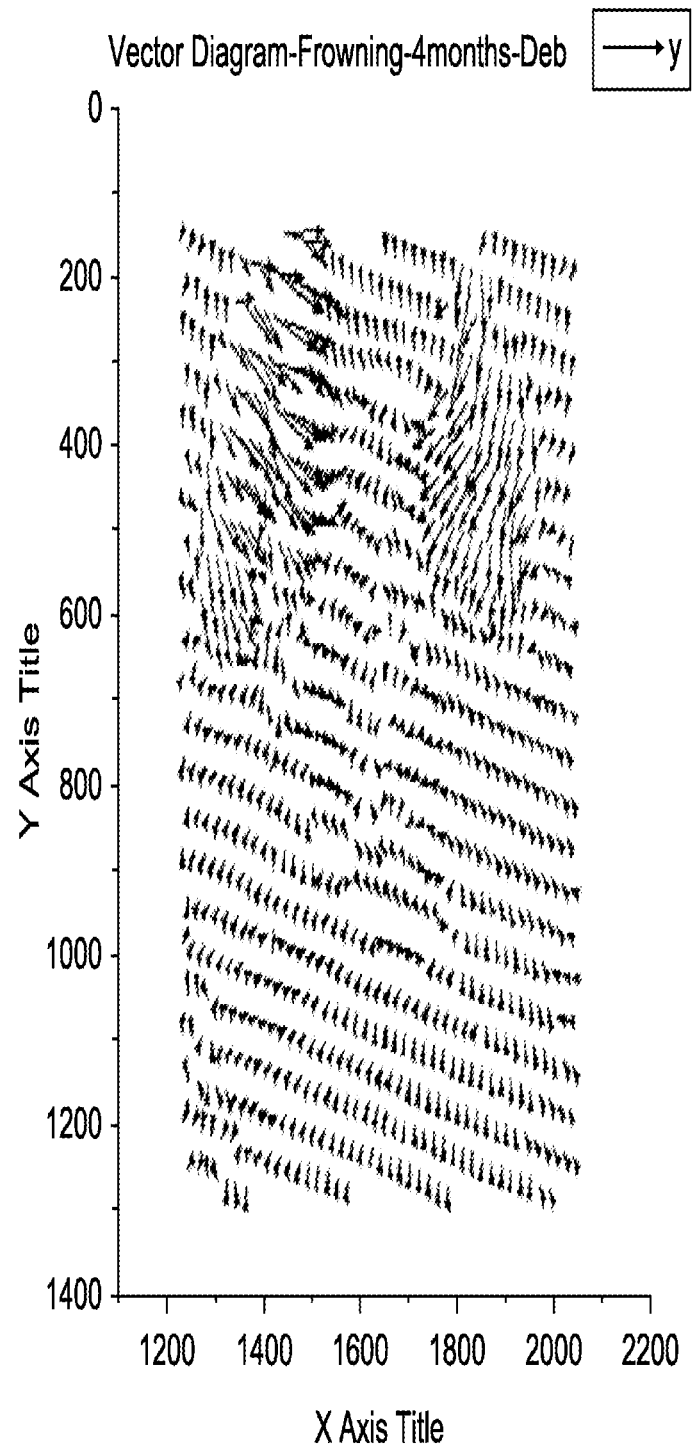
Figure 3:
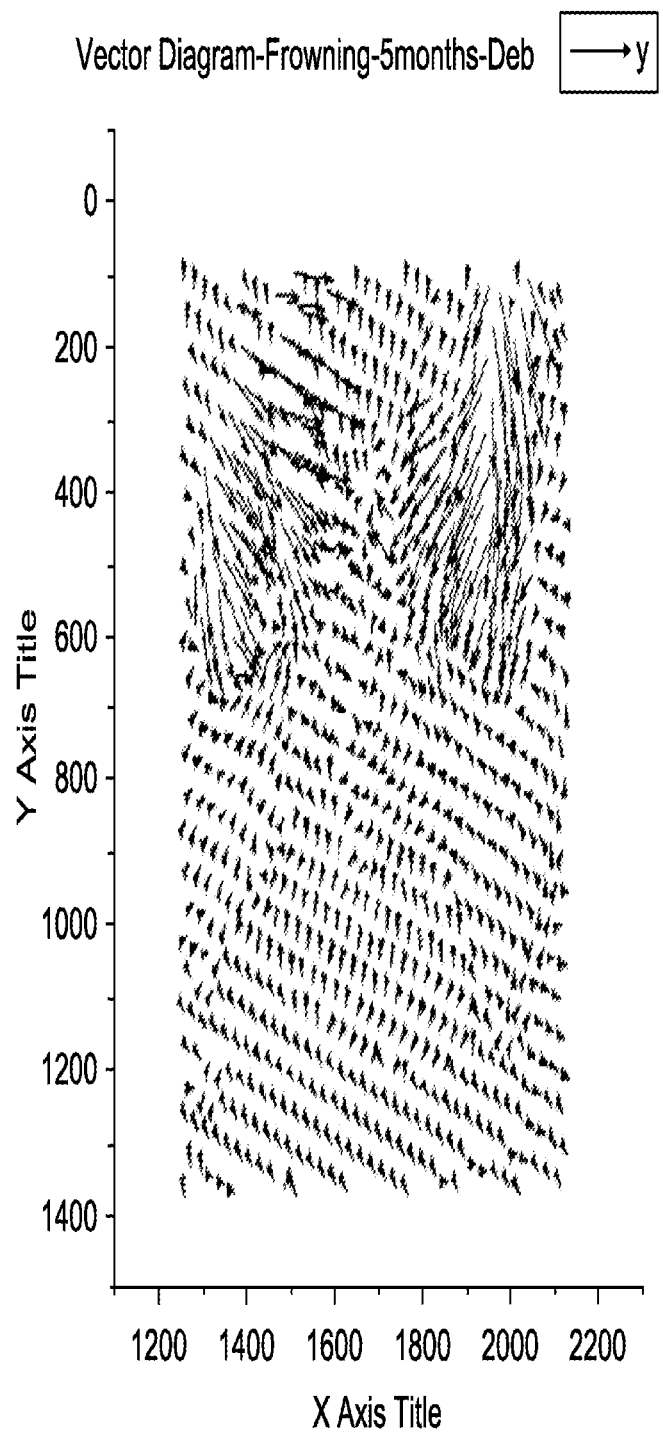
Figure 3:
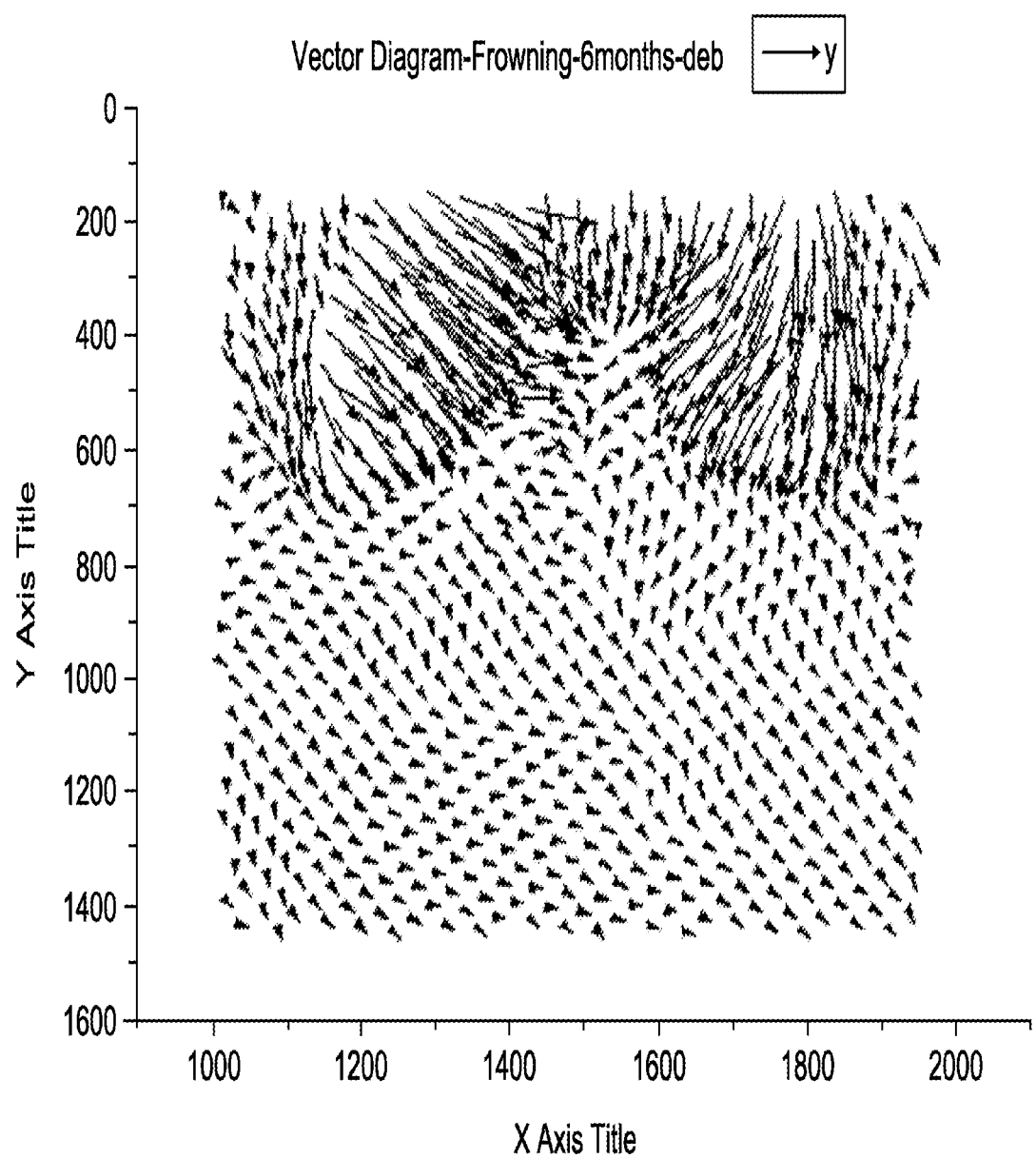
Figure 4:
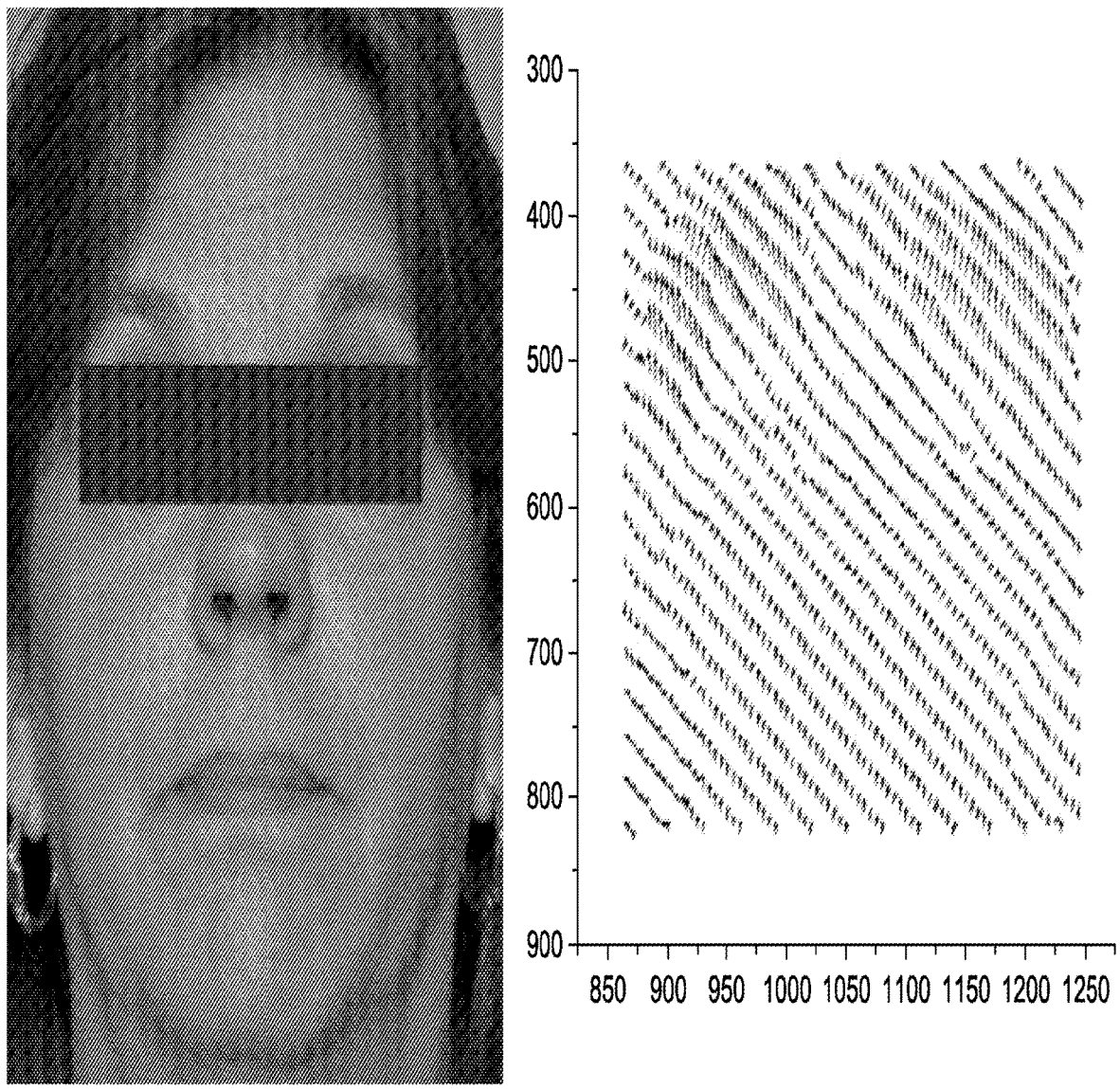
FIG. 4 shows a photograph of a patient performing another facial movement, raising her eyebrows rather than frowning, and a corresponding contour graph. One of ordinary skill in the art could overlap the photograph with the contour map to determine the location of areas of stress.
Figure 5:
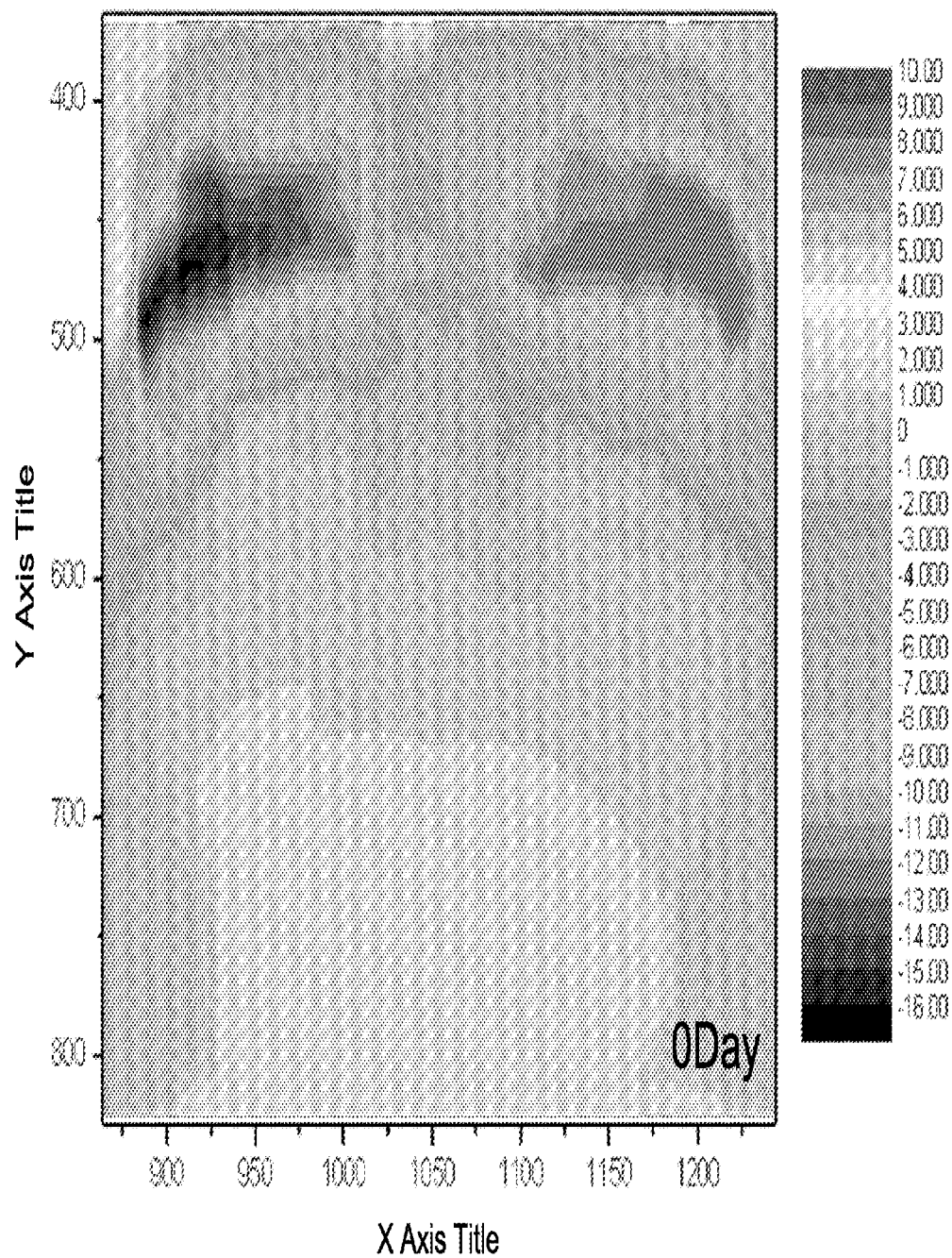
FIG. 5 includes a series of color maps generated from photographs obtained on "0Day"—before a patient received a BOTOX® injection—and 1, 2, 4, and 8 weeks afterward. Even though the black-and-white reproductions of the color figures are not as informative, one can still see the reduction in muscle contraction after the BOTOX® injection and its reemergence over time.
Figure 5:
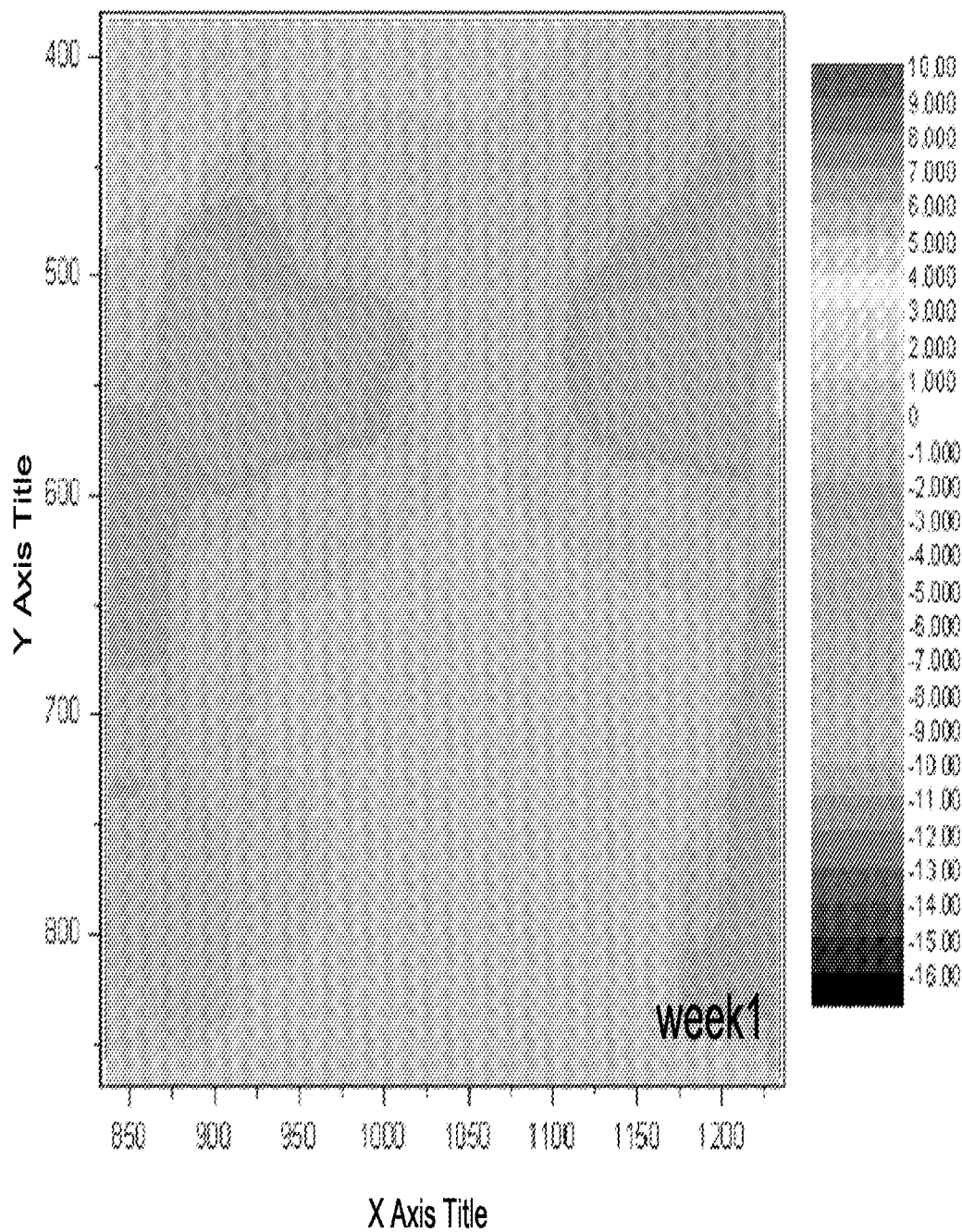
Figure 5:
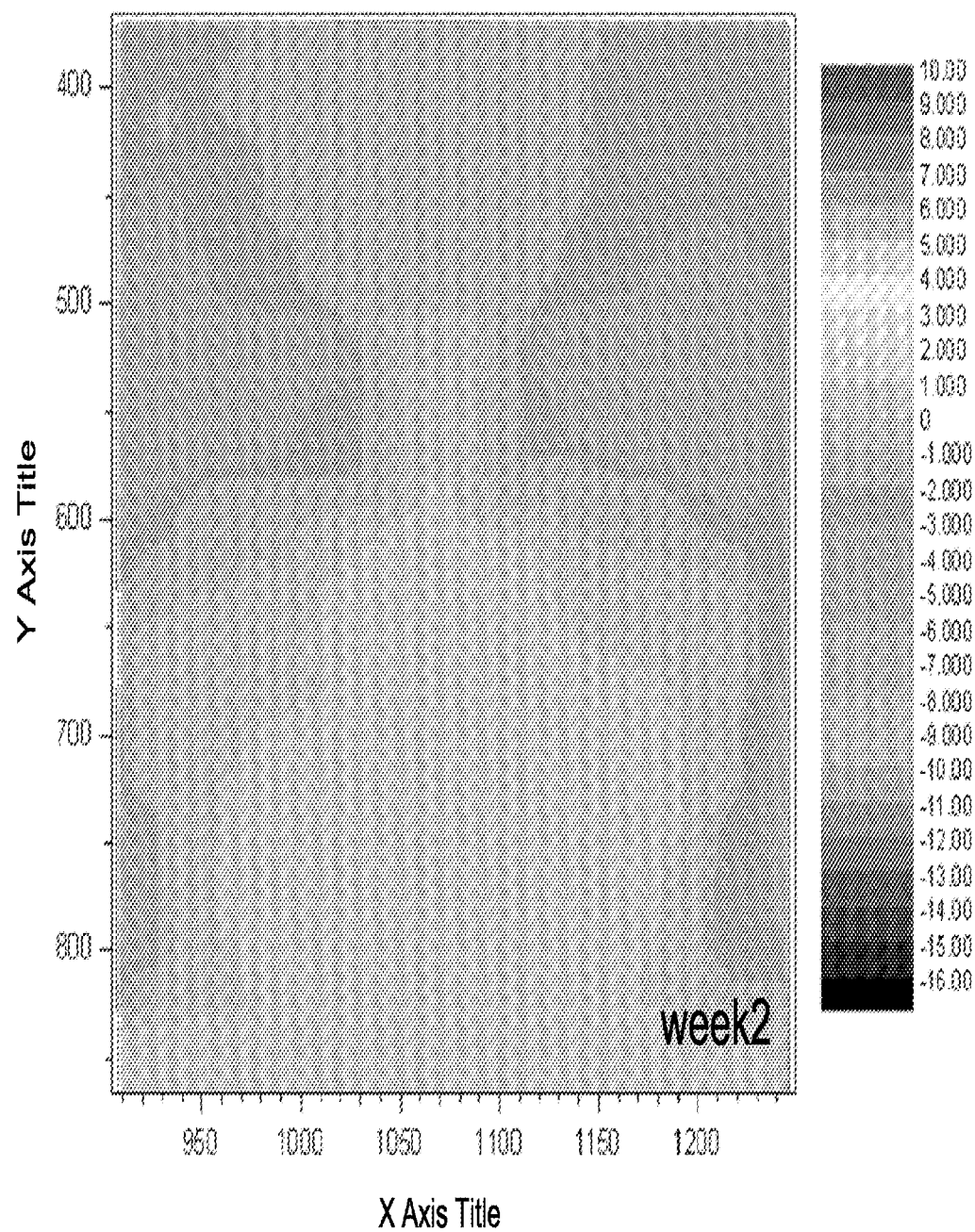
Figure 5:
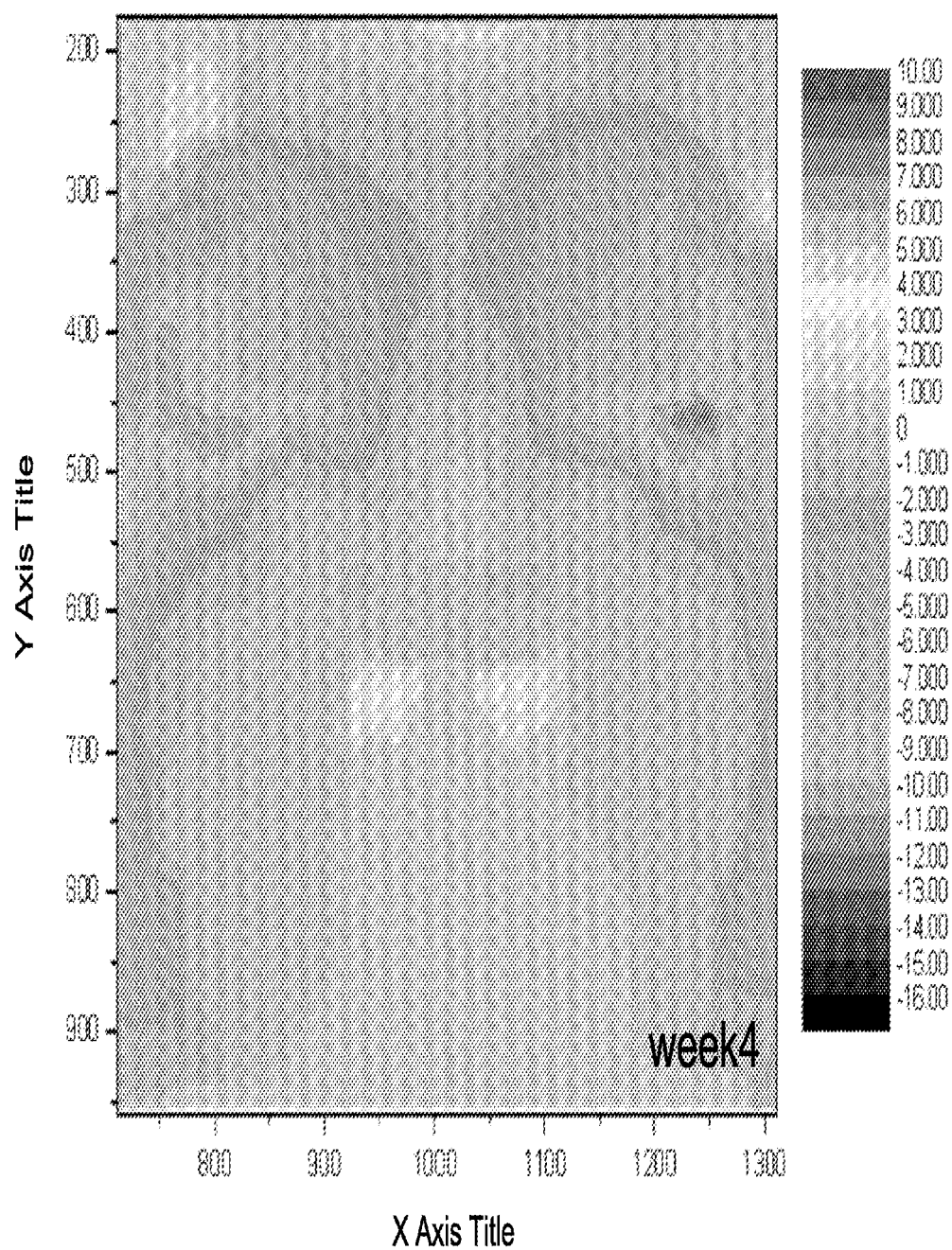
Figure 5:
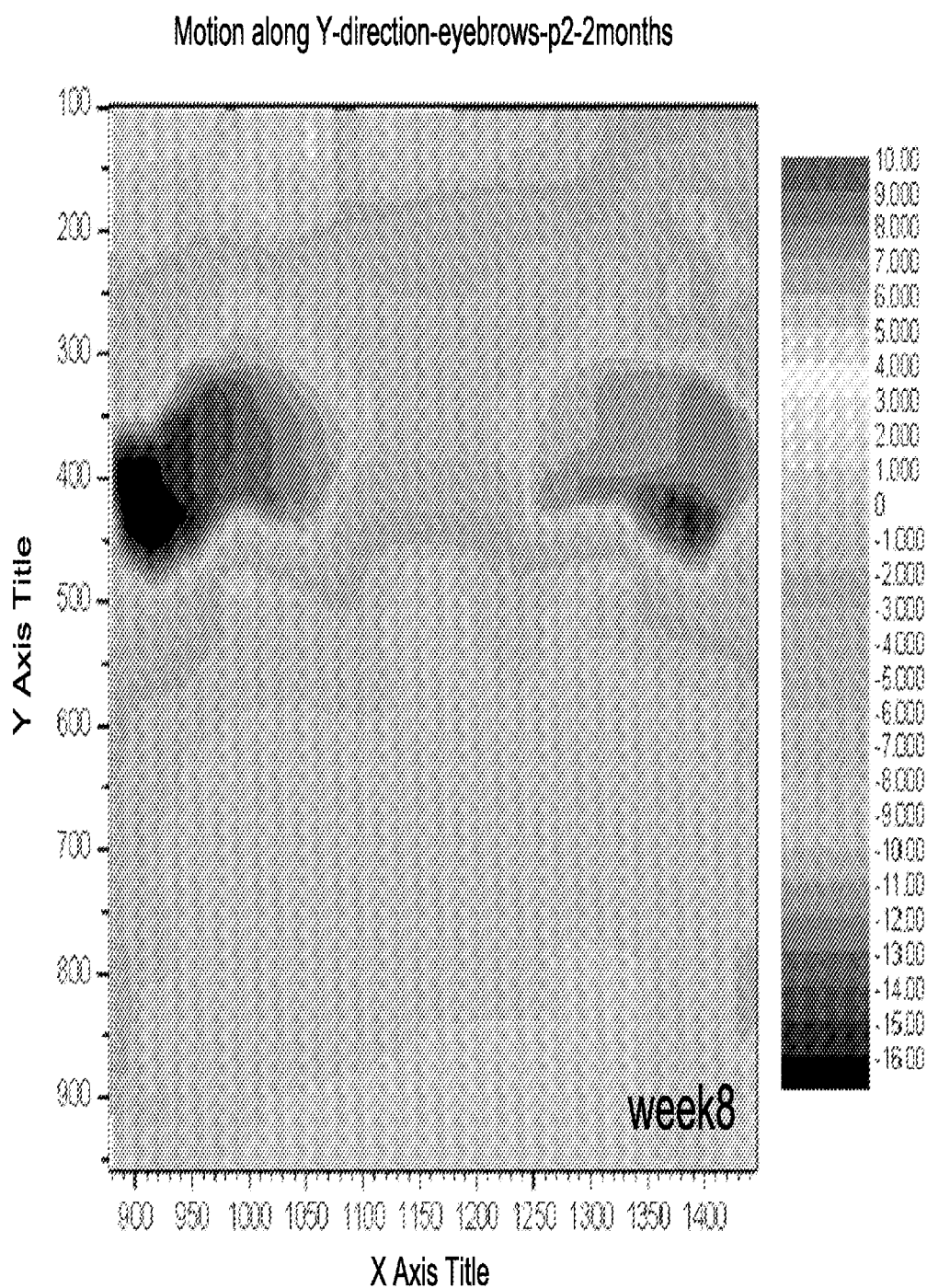
Figure 5:
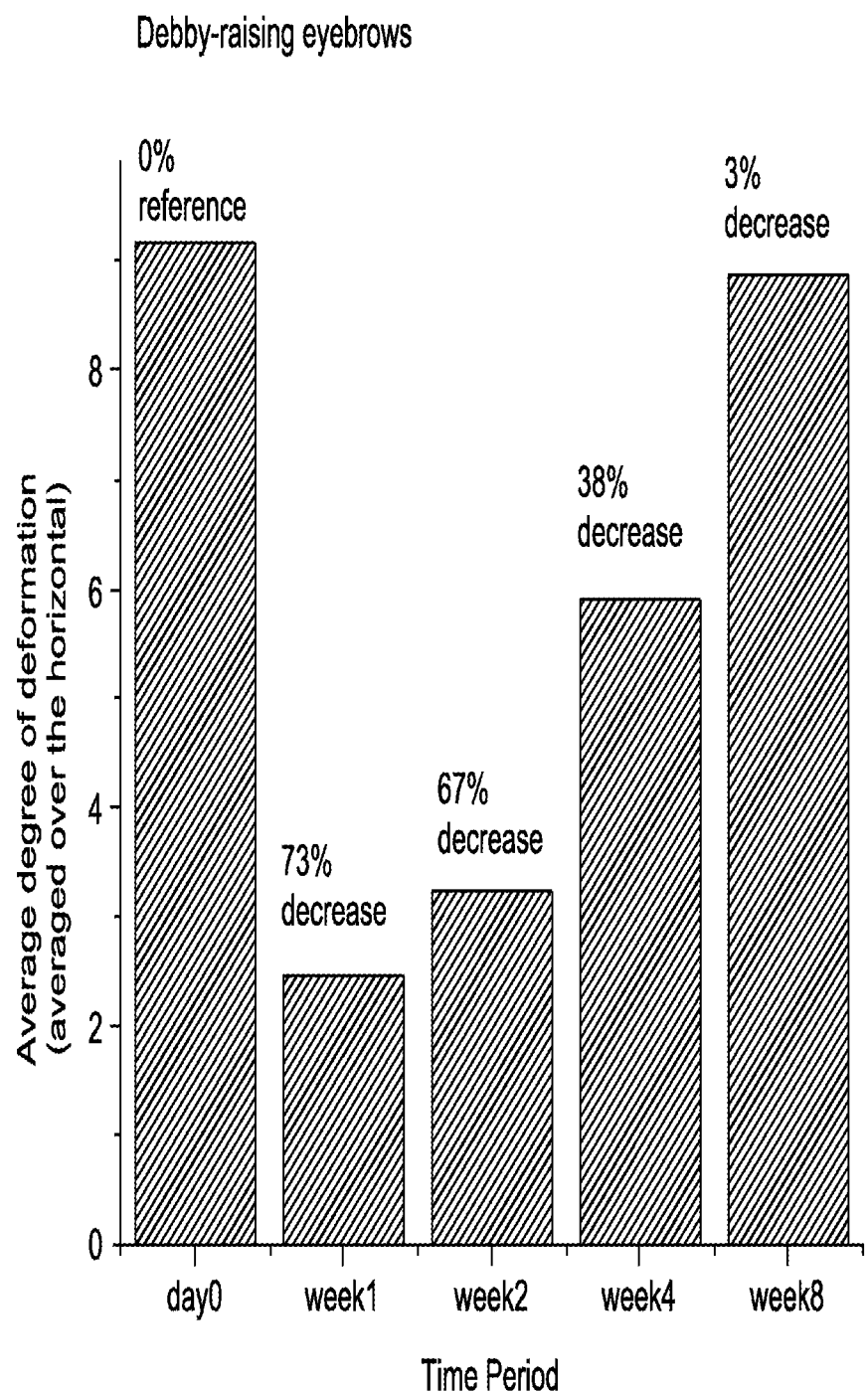

Examples of data generated from the present methods are shown in FIGS. 2-7. In addition, the following work has been conducted.

As noted above, DISC is based on following the deformation of a correlated set of speckles and generates an essentially complete mapping of the deformation of the skin pores, thereby determining the loci where stress is applied to the skin and the specific combination of muscles involved in a particular motion. Botulinum Toxin (BT) has a number of clinical applications, including cosmetic treatment of facial lines. (In the description above, we have referred to the widely used formulation of BT marketed as BOTOX®, however it is to be understood that any cosmetically acceptable agent that similarly induces paralysis could be used and analyzed by the present methods in the same manner.) Previously, the degree and duration of effects on the muscles of facial expression have been evaluated using qualitative subjective measurements (Carruthers and Carruthers, *Dermatol. Surg.* 33(1 Spec No.):S10-7, 2007). Here, we successfully quantified the initial facial muscle paralysis as well as monitored the duration of the effect of BT treatment by DISC analysis, a sensitive, non-invasive technique that derives corresponding displacement vectors through tracking geometric features on digital images before and after muscle deformation. This technology has not previously been used in conjunction with BT injection and could provide treating clinicians an insight into optimal dosing and effect duration for individual patients.

The objectives of our study were to quantify the facial muscle paralysis of each treated muscle group (forehead, glabellar complex, and crow's feet) using DISC and to determine the differences in treatment response seen among the muscle groups and the rate of return over time. Currently, we know of no useful tools to quantify the changes in facial muscle contractile strength following treatment with botulinum toxin. Vector displacement of the skin generated by DISC can help determine the site of injection to produce optimal cosmetic results. DISC analysis calculates the magnitude and vector of muscle contraction through photographic analysis and determines the point at which the toxin's effects have fully dissipated by monitoring the return of muscle contraction.

In our study protocol, we enrolled male or female patients aged 18 or older (n=6). The patients' photographs were taken pre-treatment with their faces at rest, frowning, raising their eyebrows and blinking to determine the magnitude of baseline reference for muscle motion of individual patients. We then performed injections based on PRS guidelines and physician's subjective muscle mass assessment in the glabellar complex, forehead, and crow's feet. The patients were photographed again immediately following the injections. Follow-up occurred at 1 week, 2 weeks, 4 weeks, 8 weeks, 12 weeks, 16 weeks, 20 weeks, and 24 weeks. Photographs were taken in the same way at these time points, and we performed analysis of the face at each time point in order to monitor changes in muscle contraction over time. For treatment of the glabellar complex (corrugator supercilii, procerus, depressor supercilii, and obicularis oculi), 5-7 injections were given, with males receiving 30-40 units and females receiving 10-30 units. For treatment of crow's feet (orbicularis oculi (lateral part)), 4-10 injections were given (2-5 per side). Males were injected with 6->15 units in total, and females were injected with 6-15 units in total. The results obtained from Patient 4 while frowning and raising her eyebrows prior to treatment and at specific follow up time points are shown in FIG. 8. DISC analysis demonstrated substantial facial muscle paralysis beginning at 2 weeks and varying degrees of recovery by 20 weeks, depending upon the individual muscle group. The graphs shown in FIG. 8 demonstrate the paralysis and recovery of the forehead and glabellar areas in Patient 4. The frontalis muscle, which demonstrates a dramatic decrease in contraction when Patient 4 attempts to raise her eyebrows beginning at the second week, also shows a more rapid recovery. The glabellar complex (activated by frowning) also displays a significant drop in contraction strength, with the maximum effect seen at 2 weeks post-treatment, which was greater in magnitude and slower to recover. Despite the demonstrated near recovery of the paralyzed muscles, patient perception of effect only began to decrease slightly at the 12-week time point as measured by FLO-11 (from 90.9 at week 4 to 74.5 at week 12) and no change in SPA. The DISC results were averaged by Gaussian integration to calculate the percentage change from baseline.

Vector diagrams depicting the direction of muscle contraction in the glabellar and forehead region as the patient is subjected to frowning and raising of the eyebrows are also shown in FIG. 8. Such a vector map generated by DISC analysis can give an insight into the areas where stress is directed and how it dissipates following the botulinum toxin treatment. Knowledge of the direction of the muscle contraction can help tailor the site of injection for individual patients.

DISC analysis can provide insight into the precise duration of muscle paralysis or the cumulative effects of multiple successive treatments. It can enhance clinical judgment, tailoring the amount and location of injections to the unique facial muscle profile of the patient. Additional clinical applications include monitoring the recovery after nerve repair and recording prospective outcomes data for facial transplant recipients. With its highly sensitive, non-invasive nature and ease of reproducibility, we believe DISC analysis can revolutionize outcomes measures in clinical practice.

We claim:

1. A method for identifying one or more injection sites for a cosmetic agent that induces muscle paralysis, the method comprising:
   (a) taking one or more photographs of a patient's skin in an area or areas to be treated with the cosmetic agent while the patient is at rest;
   (b) taking one or more photographs of the patient's skin in the area or areas to be treated with the cosmetic agent while the patient is performing an action;
   (c) performing digital image speckle correlation (DISC) analysis on the photographs from steps (a) and (b), thereby generating a vector diagram comprising a series of displacement vectors that each represents the movement of a pore from its at rest position to its final location;
   (d) identifying one or more locus of large stress in the vector diagram; and
   (e) identifying the location for the one or more injection sites for the cosmetic agent within the one or more locus of large stress.

2. The method of claim 1, further comprising the step of injecting the cosmetic agent at the locus of large stress.

3. The method of claim 2, wherein the steps (a) to (e) are subsequently repeated to monitor at least one effect on the skin after injection with the cosmetic agent.

4. The method of claim 3, wherein the steps (a) to (e) are repeated within 24 weeks after injection with the cosmetic agent.

5. The method of claim 1, wherein the one or more areas to be treated comprise skin of the face or neck.

6. The method of claim 1, wherein the action performed by the patient comprises smiling; moving the jaw, lips or tongue; moving the eyes; or moving the forehead.

7. The method of claim 1, wherein the one or more areas to be treated comprise skin having forehead lines, glabellar lines, or crow's feet.

8. A method for administering to a patient a cosmetic agent that induces muscle paralysis, the method comprising:
   (a) identifying one or more injection sites for the cosmetic agent comprising the steps of:
      (i) taking one or more photographs of the patient's skin in the area or areas to be treated with the cosmetic agent while the patient is at rest;
      (ii) taking one or more photographs of the patient's skin in the area or areas to be treated with the cosmetic agent while the patient is performing an action;
      (iii) performing digital image speckle correlation (DISC) analysis on the photographs from steps (a) and (b), thereby generating a vector diagram comprising a series of displacement vectors that each represents the movement of a pore from its at rest position to its final location;
      (iv) identifying one or more locus of large stress in the vector diagram; and
   (b) injecting the cosmetic agent into the one or more locus of large stress.

9. The method of claim 8, wherein the one or more areas to be treated comprise skin of the face or neck.

10. The method of claim 8, wherein the action performed by the patient comprises smiling; moving the jaw, lips or tongue; moving the eyes; or moving the forehead.

11. The method of claim 8, wherein the one or more areas to be treated comprise skin having forehead lines, glabellar lines, or crow's feet.

12. The method of claim 8, wherein the steps (a) to (e) are subsequently repeated to monitor at least one effect on the skin after injection with the cosmetic agent.

13. The method of claim 12, wherein the steps (a) to (e) are repeated within 24 weeks after injection with the cosmetic agent.

* * * * *